United States Patent
Zheng et al.

(10) Patent No.: US 10,738,078 B2
(45) Date of Patent: Aug. 11, 2020

(54) USE OF CAPRYLIC ACID PRECIPITATION FOR PROTEIN PURIFICATION

(71) Applicant: BRISTOL-MYERS SQUIBB COMPANY, Princeton, NJ (US)

(72) Inventors: Ji Zheng, Warrington, PA (US); Jue Wang, Bridgewater, NJ (US)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 112 days.

(21) Appl. No.: 15/523,632

(22) PCT Filed: Nov. 3, 2015

(86) PCT No.: PCT/US2015/058711
§ 371 (c)(1),
(2) Date: May 1, 2017

(87) PCT Pub. No.: WO2016/073401
PCT Pub. Date: May 12, 2016

(65) Prior Publication Data
US 2017/0313742 A1 Nov. 2, 2017

Related U.S. Application Data

(60) Provisional application No. 62/074,415, filed on Nov. 3, 2014.

(51) Int. Cl.
*C07K 1/22* (2006.01)
*C07K 1/36* (2006.01)
*C07K 16/06* (2006.01)
*C07K 1/18* (2006.01)
*C07K 1/32* (2006.01)

(52) U.S. Cl.
CPC ............... *C07K 1/32* (2013.01); *C07K 1/18* (2013.01); *C07K 1/22* (2013.01); *C07K 1/36* (2013.01); *C07K 16/065* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. |
| 5,223,409 A | 6/1993 | Ladner et al. |
| 5,225,539 A | 7/1993 | Winter |
| 5,367,054 A | 11/1994 | Lee |
| 5,403,484 A | 4/1995 | Ladner et al. |
| 5,427,908 A | 6/1995 | Dower et al. |
| 5,476,996 A | 12/1995 | Wilson et al. |
| 5,530,101 A | 6/1996 | Queen et al. |
| 5,534,615 A | 7/1996 | Baker et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,762 A | 12/1997 | Queen et al. |
| 5,698,767 A | 12/1997 | Wilson et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |
| 5,885,793 A | 3/1999 | Griffiths et al. |
| 5,939,598 A | 8/1999 | Kucherlapati et al. |
| 5,969,108 A | 10/1999 | McCafferty et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,172,197 B1 | 1/2001 | McCafferty et al. |
| 6,180,370 B1 | 1/2001 | Queen et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |

(Continued)

FOREIGN PATENT DOCUMENTS

| | | |
|---|---|---|
| EP | 0 893 450 | 1/1999 |
| WO | WO 92/03918 | 3/1992 |

(Continued)

OTHER PUBLICATIONS

International Preliminary Report for PCT/US2015/058711 dated May 9, 2017.
Brodsky, Y. et al., "Caprylic acid precipitation method for impurity reduction: an alternative to conventional chromatography for monoclonal antibody purification," Biotechnology and Bioengineering, vol. 109, No. 1, (Oct. 1, 2012), pp. 2589-2598.
Ahamed, T. et al., "Selection of pH-related parameters in ion-exchange chromatography using pH-gradient operations", Journal of Chromatography A, vol. 1194, pp. 22-29 (2008).
Arunakumari, A. et al., "Improved Downstream Process Design for Human Monoclonal Antibody Production", Supplement to Biopharm International, pp. 36-40 (2007).
Boschetti, E. et al., "Hydrophobic Charge-Induction Chromatography", Genetic Engineering News, vol. 20, No. 13 (2000).
Boschetti, E., "The use of thiophilic chromatography for antibody purification: a review", J. Biochem. Biophys. Methods, vol. 49, pp. 361-389 (2001).

(Continued)

*Primary Examiner* — Daniel E Kolker
*Assistant Examiner* — James L Rogers

(57) ABSTRACT

In certain embodiments, the invention provides a method of purifying a protein of interest from a mixture which comprises the protein of interest and one or more contaminants, comprising: a) subjecting the mixture to a first chromatography step; b) recovering the protein of interest in an elution solution; c) adding caprylic acid to the elution solution to form a contaminant precipitate; d) removing the contaminant precipitate from the elution solution; and e) subjecting the post-precipitated elution solution to a second chromatography column, thereby purifying the protein of interest.

11 Claims, 9 Drawing Sheets

(56) References Cited

U.S. PATENT DOCUMENTS

| | | | |
|---|---|---|---|
| 6,582,915 | B1 | 6/2003 | Griffiths et al. |
| 6,593,081 | B1 | 7/2003 | Griffiths et al. |
| 6,955,917 | B2 | 10/2005 | Alred |
| 2001/0016331 | A1 | 8/2001 | Kominami et al. |
| 2003/0152966 | A1 | 8/2003 | Alred et al. |
| 2012/0101262 | A1 | 4/2012 | Arunakumari et al. |
| 2016/0115194 | A1* | 4/2016 | Gagnon ............ C07K 1/34 530/387.1 |
| 2016/0272675 | A1* | 9/2016 | Jungbauer ............ C07K 16/00 |

FOREIGN PATENT DOCUMENTS

| | | |
|---|---|---|
| WO | WO 93/12227 | 6/1993 |
| WO | WO 94/11026 | 5/1994 |
| WO | WO 94/25585 | 11/1994 |
| WO | WO 97/12901 | 4/1997 |
| WO | WO 97/13852 | 4/1997 |
| WO | WO 98/24884 | 6/1998 |
| WO | WO 99/45962 | 9/1999 |
| WO | WO 01/14424 | 3/2001 |
| WO | WO 02/43478 | 6/2002 |
| WO | WO 06/110277 | 10/2006 |
| WO | WO 08/100578 | 8/2008 |
| WO | WO2010/151632 | 12/2010 |

OTHER PUBLICATIONS

Burton, S.C. et al., "Hydrophobic charge induction chromatography: salt independent protein adsorption and facile elution with aqueous buffers", Journal of Chromatography A, vol. 814, pp. 71-81 (1998).

Chen, J. et al., "B cell development in mice that lack one or both immunoglobulin K light chain genes", The EMBO Journal, vol. 12, No. 3, pp. 821-830 (1993).

Chen, J. et al., "Immunoglobulin gene rearrangement in B cell deficient mice generated by targeted deletion of the $J_H$ locus", International Immunology, vol. 5, No. 6, pp. 647-656 (1993).

Choi, T.K. et al., "Transgenic mice containing a human heavy chain immunoglobulin gene fragment cloned in a yeast artificial chromosome", Nature Genetics, vol. 4, pp. 117-123, and a correction p. 320 (1993).

Clackson, T. et al., "Making antibody fragments using phage display libraries", Nature, vol. 352, pp. 624-628 (1991).

De Vilmorin, P., "Scale-up Evaluation of Selective Antibody Precipitation and Continuous Recovery with a Disc-Stack Centrifuge", BioProcess International Conference & Exhibition Anaheim, CA, Sep. 23-26, 2008.

Fishwild, D.M. et al., "High-avidity human IgGκ monoclonal antibodies from a novel strain of minilocus transgenic mice", Nature Biotechnology, vol. 14, pp. 845-851 (1996).

Foster, P.R. et al., "The Kinetics of Protein Salting-Out: Precipitation of Yeast Enzymes by Ammonium Sulfate", Biotechnology and Bioengineering, vol. XVIII, pp. 545-580 (1976).

Jones, P.T. et al., "Replacing the complementarity-determining regions in a human antibody with those from a mouse", Nature, vol. 321, pp. 522-525 (1986).

Köhler, G. et al., "Continuous cultures of fused cells secreting antibody of predefined specificity", Nature, vol. 256, pp. 495-497 (1975).

Marks, J.D. et al., "By-passing Immunization—Human Antibodies from V-gene Libraries Displayed on Phage", J. Mol. Biol., vol. 222, pp. 581-597 (1991).

Matheus, S. et al., "Liquid High Concentration IgG1 Antibody Formulations by Precipitation", Journal of Pharmaceutical Sciences, vol. 98, No. 9, pp. 3043-3057 (2009).

Morrison, S.L. et al., "Chimeric human antibody molecules: Mouse antigen-binding domains with human constant region domains", Proc. Natl. Acad. Sci. USA, vol. 81, pp. 6851-6855 (1984).

Moscariello, J., "Comparison of Potential Monoclonal Antibody Purification Processes with Two Chromatography Steps", BioProcess International Conference & Exhibition, Anaheim, CA, Sep. 23-26, 2008.

Presta, L.G., "Antibody engineering", Current Opinion in Structural Biology, vol. 2, pp. 593-596 (1992).

Riechmann, L., et al. "Reshaping human antibodies for therapy", Nature, vol. 332, pp. 323-327 (1988).

Shields, C., "Advances in Single Use Capture Chromatography", BioProcess International Conference & Exhibition, Anaheim, CA, Sep. 23-26, 2008.

Taylor, L.D. et al., "A transgenic mouse that expresses a diversity of human sequence heavy and light chain immunoglobulins", Nucleic Acids Research, vol. 20, No. 23, pp. 6287-6295 (1992).

Taylor, L.D. et al., "Human immunoglobulin transgenes undergo rearrangement, somatic mutation and class switching in mice that lack endogenous IgM", International Immunology, vol. 6, No. 4, pp. 579-591 (1994).

Tuaillon, N. et al., "Biased Utilization of $D_{HQ52}$ and $J_H4$ Gene Segments in a Human Ig Transgenic Minilocus Is Independent of Antigenic Selection", Journal of Immunology, vol. 152, pp. 2912-2920 (1994).

Tuaillon, N. et al., "Human immunoglobulin heavy-chain minilocus recombination in transgenic mice: Gene-segment use in μ and γ transcripts", Proc. Natl. Acad. Sci. USA, vol. 90, pp. 3720-3724 (1993).

Wang, J. et al., "Optimizing the Primary Recovery Step in Nonaffinity Purification Schemes for HuMAbs", BioPharm International, pp. 1-9 (2008).

Wang, L. et al., "Purification of human IgG using membrane based hybrid bioseparation technique and its variants: A comparative study", Separation and Purification Technology, vol. 66, pp. 242-247 (2009).

Zellner, M. et al., "Quantitative validation of different protein precipitation methods in proteome analysis of blood platelets", Electrophoresis, vol. 26, pp. 2481-2489 (2005).

Gagnon, P., "Use of Hydrophobic Interaction Chromatography With a Non-Salt Buffer System for Improving Process Economics in Purification of Monoclonal Antibodies", Waterside Conference on Monoclonal and Recombinant Antibodies, Miami, Florida, Tosoh, pp. 1-4, (2000).

Hanania et al., "Automated in Situ Measurement of Cell-Specific Antibody Secretion and Laser-Mediated Purification for Rapid Cloning of Highly-Secreting Producers," Biotechnology 91(7), pp. 872-876 (2005).

Glynn, J., Mar. 2, 2008, BioPharm International.com, Process-Scale Precipitation of Impurities in Mammalian Cell Culture Broth http://www.biopharminternational.com/biopharm/article/articleDetail.jsp?id=499144.

\* cited by examiner

USE OF CAPRYLIC ACID PRECIPITATION FOR PROTEIN PURIFICATION

CROSS REFERENCE TO RELATED APPLICATIONS

This application is a national phase application under 35 U.S.C. § 371 of International Patent Application No. PCT/US2015/058711, filed Nov. 3, 2015, which claims priority to U.S. Provisional Application 62/074,415, filed Nov. 3, 2014, each of which is hereby incorporated by reference in its entirety.

BACKGROUND OF THE INVENTION

The large-scale, economic purification of proteins is an increasingly important problem for the biopharmaceutical industry. Therapeutic proteins are typically produced using prokaryotic or eukaryotic cell lines that are engineered to express the protein of interest from a recombinant plasmid containing the gene encoding the protein. Separation of the desired protein from the mixture of components fed to the cells and cellular by-products to an adequate purity, e.g., sufficient for use as a human therapeutic, poses a formidable challenge to biologics manufacturers.

Accordingly, there is a need in the art for alternative protein purification methods that can be used to expedite the large-scale processing of protein-based therapeutics, such as antibodies especially due to escalating high titers from cell culture.

SUMMARY OF THE INVENTION

In certain embodiments, the present invention provides a method of purifying a protein of interest from a mixture which comprises the protein of interest and one or more contaminants, comprising: a) subjecting the mixture to a first chromatography step; b) recovering the protein of interest in an elution solution; c) adding caprylic acid to the elution solution to form a contaminant precipitate; d) removing the contaminant precipitate from the elution solution; and e) subjecting the post-precipitated elution solution to a second chromatography column, thereby purifying the protein of interest.

To illustrate, the mixture is selected from a harvested cell culture fluid, a cell culture supernatant, and a conditioned cell culture supernatant, a cell lysate, and a clarified bulk. For example, the mixture comprises contaminants selected from host cell proteins, host cell metabolites, host cell constitutive proteins, nucleic acids, endotoxins, viruses, product related contaminants, lipids, media additives and media derivatives. In a specific embodiment, the cell culture is a mammalian cell culture, such as a Chinese Hamster Ovary (CHO) cell culture. In certain embodiments, the protein of interest is an antibody, such as a monoclonal antibody (e.g., a human, humanized and chimeric antibody).

In certain embodiments, the first chromatography is selected from an affinity chromatography (e.g., a protein A affinity chromatography), an ion exchange chromatography (e.g., an anion exchange chromatography or a cation exchange chromatography), a hydrophobic interaction chromatography, and a mix-mode chromatography. In certain embodiments, the second chromatography is an ion exchange chromatography (e.g., a cation exchange chromatography or an anion exchange chromatography), a hydrophobic interaction chromatography, a mix-mode chromatography, a positive-charged membrane chromatography, and a hydrophobic interaction membrane chromatography. In a specific embodiment, the first chromatography is an affinity chromatography (e.g., a protein A affinity chromatography), and the second chromatography is an ion exchange chromatography (e.g., an anion exchange chromatography or a cation exchange chromatography). Optionally, the mixture is subjected to two chromatography steps (the first chromatography and the second chromatography), and not subjected to an additional chromatography step.

Optionally, the contaminant precipitate is removed by centrifugation, sterile filtration, depth filtration or tangential flow filtration. Optionally, the pH of the elution solution is between about 3 and 7, and preferably between 5 and 6. Optionally, the pH of the elution solution is adjusted before or after the addition of caprylic acid. Optionally, the final concentration of the caprylic acid is at least 0.05% (v/v). To illustrate, the final concentration of the caprylic acid is between about 0.05 and 20% (v/v), and preferably between about 0.5 and 1% (v/v). Optionally, the contaminant precipitate is allowed to form for at least 5 minutes, such as between about 5 to 120 minutes (e.g., 30-60 minutes) after addition of the caprylic acid.

DETAILED DESCRIPTION OF THE INVENTION

Figure 1:
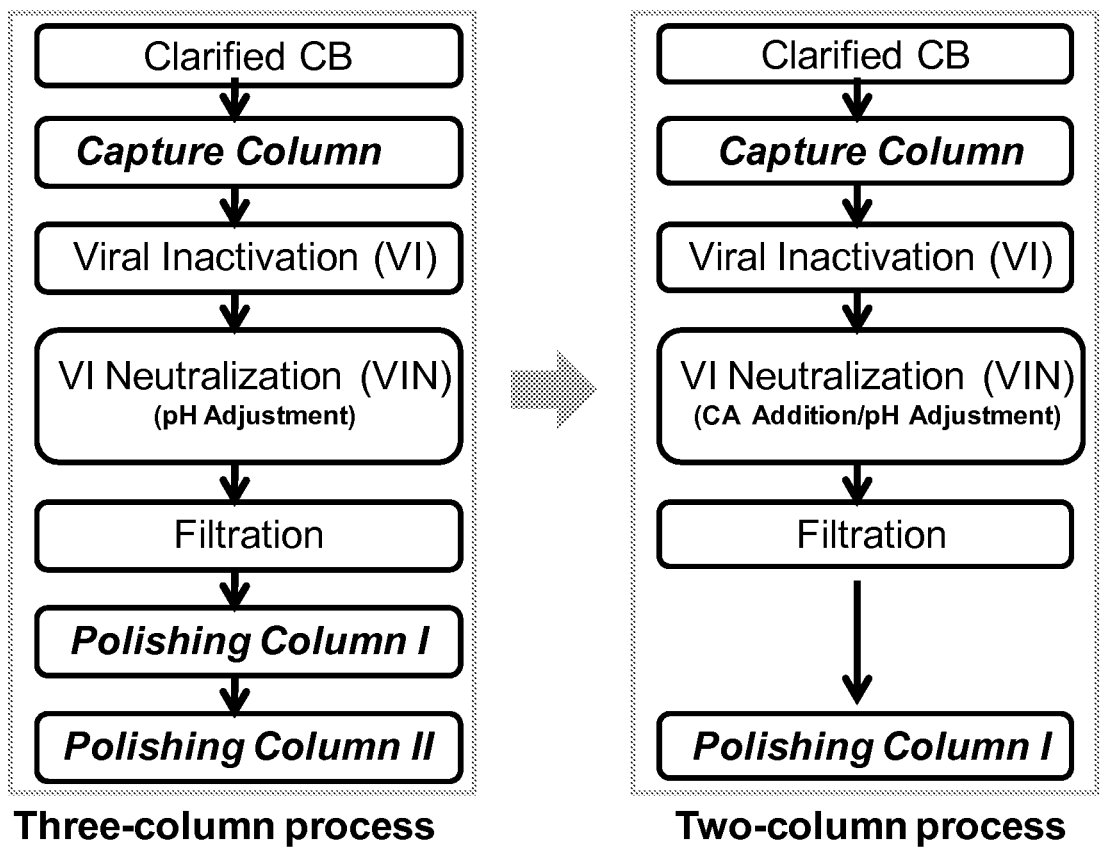
FIG. 1 shows a scheme of monoclonal antibody downstream purification process with three-chromatography step or two-chromatography step. CB: cell culture broth; VI: viral inactivation at pH 3-4; VIN: pH adjustment post low pH viral inactivation step for loading onto the first polishing column; CA: caprylic acid.

The present invention provides a protein purification method which utilizes a caprylic acid-based impurity precipitation step between two chromatography steps (e.g., a protein A capture column and an ion exchange polishing column) Such method can be used as a robust downstream process for purifying proteins, such as monoclonal antibodies with a broad range of isoelectric points (pI).

In particular, the present invention relates to a caprylic acid-based precipitation of a mixture which has been partially purified by a first chromatography step. For example, caprylic acid is added to a mixture which has been subjected to a first chromatography step (i.e., the elution collected from the first chromatography). WO 2010/151632 describes a protein purification method which involves a caprylic acid-based precipitation step before the mixture is subjected to any chromatography step. The present invention is an improvement over the method of WO 2010/151632 and is advantageous for at least the following reasons. The mixture to be precipitated has a lower level of contaminants and results in a lower level of a contaminant precipitate after caprylic acid is added, thereby significantly reducing the burden on the subsequent removal of the contaminant precipitate (e.g., by filtration methods).

In certain embodiments, the present invention provides a method of purifying a protein of interest from a mixture which comprises the protein of interest and one or more contaminants, comprising: a) subjecting the mixture to a first chromatography step; b) recovering the protein of interest in an elution solution; c) adding caprylic acid to the elution solution to form a contaminant precipitate; d) removing the contaminant precipitate from the elution solution; and e) subjecting the post-precipitated elution solution to a second chromatography column, thereby purifying the protein of interest.

To illustrate, the mixture is selected from a harvested cell culture fluid, a cell culture supernatant, and a conditioned cell culture supernatant, a cell lysate, and a clarified bulk. For example, the mixture comprises contaminants selected from host cell proteins, host cell metabolites, host cell constitutive proteins, nucleic acids, endotoxins, viruses, product related contaminants, lipids, media additives and media derivatives. In a specific embodiment, the cell culture is a mammalian cell culture, such as a Chinese Hamster Ovary (CHO) cell culture. In certain embodiments, the protein of interest is an antibody, such as a monoclonal antibody (e.g., a human, humanized and chimeric antibody).

In certain embodiments, the first chromatography is selected from an affinity chromatography (e.g., a protein A affinity chromatography), an ion exchange chromatography (e.g., an anion exchange chromatography or a cation exchange chromatography), a hydrophobic interaction chromatography, and a mix-mode chromatography. In certain embodiments, the second chromatography is an ion exchange chromatography (e.g., a cation exchange chromatography or an anion exchange chromatography), a hydrophobic interaction chromatography, a mix-mode chromatography, a positive-charged membrane chromatography, and a hydrophobic interaction membrane chromatography. In a specific embodiment, the first chromatography is an affinity chromatography (e.g., a protein A affinity chromatography), and the second chromatography is an ion exchange chromatography (e.g., an anion exchange chromatography or a cation exchange chromatography). Optionally, the mixture is subjected to two chromatography steps (the first chromatography and the second chromatography), and not subjected to an additional chromatography step.

Optionally, the contaminant precipitate is removed by centrifugation, sterile filtration, depth filtration or tangential flow filtration. Optionally, the pH of the elution solution is between about 3 and 7, and preferably between 5 and 6. Optionally, the pH of the elution solution is adjusted before or after the addition of caprylic acid. Optionally, the final concentration of the caprylic acid is at least 0.05% (v/v). To illustrate, the final concentration of the caprylic acid is between about 0.05 and 20% (v/v), and preferably between about 0.5 and 1% (v/v). Optionally, the contaminant precipitate is allowed to form for at least 5 minutes, such as between about 5 to 120 minutes (e.g., 30-60 minutes) after addition of the caprylic acid.

I. Definitions

In order that the present disclosure may be more readily understood, certain terms are first defined. As used in this application, except as otherwise expressly provided herein, each of the following terms shall have the meaning set forth below. Additional definitions are set forth throughout the application.

As used herein the term "caprylic acid" refers to octanoic acid, or any derivatives or its salt thereof capable of selectively precipitating a contaminant when added to a solution.

As used herein, the term "protein of interest" is used in its broadest sense to include any protein (either natural or recombinant), present in a mixture, for which purification is desired. Such proteins of interest include, without limitation, hormones, growth factors, cyotokines, immunoglobulins (e.g., antibodies), and immunoglobulin-like domain-containing molecules (e.g., ankyrin or fibronectin domain-containing molecules).

As used herein, a "cell culture" refers to cells in a liquid medium. Optionally, the cell culture is contained in a bioreactor. The cells in a cell culture can be from any organism including, for example, bacteria, fungus, insects, mammals or plants. In a particular embodiment, the cells in a cell culture include cells transfected with an expression construct containing a nucleic acid that encodes a protein of interest (e.g., an antibody). Suitable liquid media include, for example, nutrient media and non-nutrient media. In a particular embodiment, the cell culture comprises a Chinese Hamster Ovary (CHO) cell line in nutrient media, not subject to purification by, for example, filtration or centrifugation.

As used herein, the term "clarified bulk" refers to a mixture from which particulate matter has been substantially removed. Clarified bulk includes cell culture, or cell lysate from which cells or cell debris has been substantially removed by, for example, filtration or centrifugation.

As used herein "bioreactor" takes its art recognized meaning and refers to a chamber designed for the controlled growth of a cell culture. The bioreactor can be of any size as long as it is useful for the culturing of cells, e.g., mammalian cells. Typically, the bioreactor will be at least 30 ml and may be at least 1, 10, 100, 250, 500, 1000, 2500, 5000, 8000, 10,000, 12,0000 liters or more, or any intermediate volume. The internal conditions of the bioreactor, including but not limited to pH and temperature, are typically controlled during the culturing period. A suitable bioreactor may be composed of (i.e., constructed of) any material that is suitable for holding cell cultures suspended in media under the culture conditions and is conductive to cell growth and viability, including glass, plastic or metal; the material(s)

should not interfere with expression or stability of a protein of interest. One of ordinary skill in the art will be aware of, and will be able to choose, suitable bioreactors for use in practicing the present invention.

As used herein, a "mixture" comprises a protein of interest (for which purification is desired) and one or more contaminant, i.e., impurities. In one embodiment, the mixture is produced from a host cell or organism that expresses the protein of interest (either naturally or recombinantly). Such mixtures include, for example, cell cultures, cell lysates, and clarified bulk (e.g., clarified cell culture supernatant).

As used herein, the terms "separating" and "purifying" are used interchangeably, and refer to the selective removal of contaminants from a mixture containing a protein of interest (e.g., an antibody). The invention achieves this by precipitation of the contaminants using caprylic acid. Following precipitation, the contaminant precipitate can be removed from the mixture using any means compatible with the present invention, including common industrial methods such as centrifugation or filtration. This separation results in the recovery of a mixture with a substantially reduced level of contaminants, and thereby serves to increase the purity of the protein of interest (e.g., an antibody) in the mixture.

As used herein, the term "contaminant precipitate" refers to an insoluble substance comprising one or more contaminants formed in a solution due to the addition of a compound (e.g., caprylic acid) to the solution.

As used herein the term "contaminant" is used in its broadest sense to cover any undesired component or compound within a mixture. In cell cultures, cell lysates, or clarified bulk (e.g., clarified cell culture supernatant), contaminants include, for example, host cell nucleic acids (e.g., DNA) and host cell proteins present in a cell culture medium. Host cell contaminant proteins include, without limitation, those naturally or recombinantly produced by the host cell, as well as proteins related to or derived from the protein of interest (e.g., proteolytic fragments) and other process related contaminants. In certain embodiments, the contaminant precipitate is separated from the cell culture using an art-recognized means, such as centrifugation, sterile filtration, depth filtration and tangential flow filtration.

As used herein "centrifugation" is a process that involves the use of the centrifugal force for the sedimentation of heterogeneous mixtures with a centrifuge, used in industry and in laboratory settings. This process is used to separate two immiscible liquids. For example, in a method of the present invention, centrifugation can be used to remove a contaminant precipitation from a mixture, including without limitation, a cell culture or clarified cell culture supernatant or capture-column captured elution pool.

As used herein "sterile filtration" is a filtration method that use membrane filters, which are typically a filter with pore size 0.2 µm to effectively remove microorganisms or small particles. For example, in a method of the present invention, sterile filtration can be used to remove a contaminant precipitate from a mixture, including without limitation, a cell culture or clarified cell culture supernatant or capture-column captured elution pool.

As used herein "depth filtration" is a filtration method that uses depth filters, which are typically characterized by their design to retain particles due to a range of pore sizes within a filter matrix. The depth filter's capacity is typically defined by the depth, e.g., 10 inch or 20 inch of the matrix and thus the holding capacity for solids. For example, in a method of the present invention, depth filtration can be used to remove a contaminant precipitate from a mixture, including without limitation, a cell culture or clarified cell culture supernatant or capture-column captured elution pool.

As used herein, the term "tangential flow filtration" refers to a filtration process in which the sample mixture circulates across the top of a membrane, while applied pressure causes certain solutes and small molecules to pass through the membrane. For example, in a method of the present invention, tangential flow filtration can be used to remove a contaminant precipitate from a mixture, including without limitation, a cell culture or clarified cell culture supernatant or capture-column captured elution pool.

As used herein the term "chromatography" refers to the process by which a solute of interest, e.g., a protein of interest, in a mixture is separated from other solutes in the mixture by percolation of the mixture through an adsorbent, which adsorbs or retains a solute more or less strongly due to properties of the solute, such as pI, hydrophobicity, size and structure, under particular buffering conditions of the process. In a method of the present invention, chromatography can be used to remove contaminants after the precipitate is removed from a mixture, including without limitation, a cell culture or clarified cell culture supernatant or capture-column captured elution pool.

The terms "ion-exchange" and "ion-exchange chromatography" refer to a chromatographic process in which an ionizable solute of interest (e.g., a protein of interest in a mixture) interacts with an oppositely charged ligand linked (e.g., by covalent attachment) to a solid phase ion exchange material under appropriate conditions of pH and conductivity, such that the solute of interest interacts non-specifically with the charged compound more or less than the solute impurities or contaminants in the mixture. The contaminating solutes in the mixture can be washed from a column of the ion exchange material or are bound to or excluded from the resin, faster or slower than the solute of interest. "Ion-exchange chromatography" specifically includes cation exchange, anion exchange, and mixed mode chromatographies.

The phrase "ion exchange material" refers to a solid phase that is negatively charged (i.e., a cation exchange resin or membrane) or positively charged (i.e., an anion exchange resin or membrane). In one embodiment, the charge can be provided by attaching one or more charged ligands (or adsorbents) to the solid phase, e.g., by covalent linking. Alternatively, or in addition, the charge can be an inherent property of the solid phase (e.g., as is the case for silica, which has an overall negative charge).

A "cation exchange resin" refers to a solid phase which is negatively charged, and which has free cations for exchange with cations in an aqueous solution passed over or through the solid phase. Any negatively charged ligand attached to the solid phase suitable to form the cation exchange resin can be used, e.g., a carboxylate, sulfonate and others as described below. Commercially available cation exchange resins include, but are not limited to, for example, those having a sulfonate based group (e.g., MonoS, MiniS, Source 15S and 30S, SP SEPHAROSE® Fast Flow, SP SEPHAROSE® High Performance from GE Healthcare, TOYOPEARL® SP-650S and SP-650M from Tosoh, MACRO-PREP® High S from BioRad, Ceramic HyperD S, TRISACRYL® M and LS SP and Spherodex LS SP from Pall Technologies); a sulfoethyl based group (e.g., FRACTOGEL® SE, from EMD, POROS® S-10 and S-20 from Applied Biosystems); a sulphopropyl based group (e.g., TSK Gel SP 5PW and SP-5PW-HR from Tosoh, POROS® HS-20 and HS 50 from Applied Biosystems); a sulfoisobutyl based group (e.g., FRACTOGEL® EMD $SO_3^-$ from EMD);

a sulfoxyethyl based group (e.g., SE52, SE53 and Express-Ion S from Whatman), a carboxymethyl based group (e.g., CM SEPHAROSE® Fast Flow from GE Healthcare, Hydrocell CM from Biochrom Labs Inc., MACRO-PREP® CM from BioRad, Ceramic HyperD CM, TRISACRYL® M CM, TRISACRYL® LS CM, from Pall Technologies, Matrx CELLUFINE® C500 and C200 from Millipore, CM52, CM32, CM23 and Express—Ion C from Whatman, TOYO-PEARL® CM-650S, CM-650M and CM-650C from Tosoh); sulfonic and carboxylic acid based groups (e.g., BAKERBOND® Carboxy-Sulfon from J. T. Baker); a carboxylic acid based group (e.g., WP CBX from J. T Baker, DOWEX® MAC-3 from Dow Liquid Separations, AMBERLITE® Weak Cation Exchangers, DOWEX® Weak Cation Exchanger, and DIAION® Weak Cation Exchangers from Sigma-Aldrich and FRACTOGEL® EMD COO— from EMD); a sulfonic acid based group (e.g., Hydrocell SP from Biochrom Labs Inc., DOWEX® Fine Mesh Strong Acid Cation Resin from Dow Liquid Separations, UNOsphere S, WP Sulfonic from J. T. Baker, SARTOBIND® S membrane from Sartorius, AMBERLITE® Strong Cation Exchangers, DOWEX® Strong Cation and DIAION® Strong Cation Exchanger from Sigma-Aldrich); and a orthophosphate based group (e.g., P11 from Whatman).

An "anion exchange resin" refers to a solid phase which is positively charged, thus having one or more positively charged ligands attached thereto. Any positively charged ligand attached to the solid phase suitable to form the anionic exchange resin can be used, such as quaternary amino groups Commercially available anion exchange resins include DEAE cellulose, POROS® PI 20, PI 50, HQ 10, HQ 20, HQ 50, D 50 from Applied Biosystems, SARTOBIND® Q from Sartorius, MonoQ, MiniQ, Source 15Q and 30Q, Q, DEAE and ANX SEPHAROSE® Fast Flow, Q SEPHAROSE® high Performance, QAE SEPHADEX® and FAST Q SEPHAROSE® (GE Healthcare), WP PEI, WP DEAM, WP QUAT from J. T. Baker, Hydrocell DEAE and Hydrocell QA from Biochrom Labs Inc., UNOsphere Q, MACRO-PREP® DEAE and MACRO-PREP® High Q from Biorad, Ceramic HyperD Q, ceramic HyperD DEAE, TRISACRYL® M and LS DEAE, Spherodex LS DEAE, QMA SPHEROSIL® LS, QMA SPHEROSIL® M and MUSTANG® Q from Pall Technologies, DOWEX® Fine Mesh Strong Base Type I and Type II Anion Resins and DOWEX® MONOSPHER E 77, weak base anion from Dow Liquid Separations, INTERCEPT® Q membrane, Matrex CELLUFINE® A200, A500, Q500, and Q800, from Millipore, FRACTOGEL® EMD TMAE, FRACTOGEL® EMD DEAE and FRACTOGEL® EMD DMAE from EMD, AMBERLITE® weak strong anion exchangers type I and II, DOWEX® weak and strong anion exchangers type I and II, DIAION® weak and strong anion exchangers type I and II, DUOLITE® from Sigma-Aldrich, TSK gel Q and DEAE 5PW and 5PW-HR, TOYOPEARL® SuperQ-650S, 650M and 650C, QAE-550C and 650S, DEAE-650M and 650C from Tosoh, QA52, DE23, DE32, DE51, DE52, DE53, Express-Ion D and Express-Ion Q from Whatman, and SARTOBIND® Q (Sartorius corporation, New York, USA).

A "mixed mode ion exchange resin" or "mixed mode" refers to a solid phase which is covalently modified with cationic, anionic, and/or hydrophobic moieties. Examples of mixed mode ion exchange resins include BAKERBOND® ABX (J. T. Baker; Phillipsburg, N.J.), ceramic hydroxyapatite type I and II and fluoride hydroxyapatite (BioRad; Hercules, Calif.) and MEP and MBI HyperCel (Pall Corporation; East Hills, N.Y.).

A "hydrophobic interaction chromatography resin" refers to a solid phase which is covalently modified with phenyl, octyl, or butyl chemicals. Hydrophobic interaction chromatography is a separation technique that uses the properties of hydrophobicity to separate proteins from one another. In this type of chromatography, hydrophobic groups such as, phenyl, octyl, or butyl are attached to the stationary column. Proteins that pass through the column that have hydrophobic amino acid side chains on their surfaces are able to interact with and bind to the hydrophobic groups on the column. Examples of hydrophobic interaction chromatography resins include: (1) Butyl FF, Butyl HP, Octyl FF, Phenyl FF, Phenyl HP, Phenyl FF (high sub), Phenyl FF (low sub), Capto Phenyl ImpRes, Capto Phenyl (high sub), Capto Octyl, Capto ButylImpRes, Capto Butyl (GE Healthcare, Uppsala, Sweden); (2) TOYOPEARL® Super Butyl-550C, TOYOPEARL® Hexyl-650C, Butyl-650C, Phenyl-650C, Butyl 600 M, Phenyl-600M, PPG-600M, Butyl-650M, Phenyl-650M, Ether-650M, Butyl-650S, Phenyl-650S, Ether-650S, TSKgel Pheny-5PW, TSKgel Ether-5PW (Tosoh Bioscience, Tokyo, Japan); (3) MACRO-PREP®-butyl, MACRO-PREP®-methyl (Bio-Rad); and (4) SARTOBIND® Phenyl (Sartorius corporation, New York, USA).

II. Proteins of Interest

In certain aspects, methods of the present invention may be used to purify any protein of interest including, but not limited to, proteins having pharmaceutical, diagnostic, agricultural, and/or any of a variety of other properties that are useful in commercial, experimental or other applications. In addition, a protein of interest can be a protein therapeutic. In certain embodiments, proteins purified using methods of the present invention may be processed or modified. For example, a protein of interest in accordance with the present invention may be glycosylated.

Thus, the present invention may be used to culture cells for production of any therapeutic protein, such as pharmaceutically or commercially relevant enzymes, receptors, receptor fusion proteins, antibodies (e.g., monoclonal or polyclonal antibodies), antigen-binding fragments of an antibody, Fc fusion proteins, cytokines, hormones, regulatory factors, growth factors, coagulation/clotting factors, or antigen-binding agents. The above list of proteins is merely exemplary in nature, and is not intended to be a limiting recitation. One of ordinary skill in the art will know that other proteins can be produced in accordance with the present invention, and will be able to use methods disclosed herein to produce such proteins.

In one particular embodiment of the invention, the protein purified using the method of the invention is an antibody. The term "antibody" is used in the broadest sense to cover monoclonal antibodies (including full length monoclonal antibodies), polyclonal antibodies, multispecific antibodies (e.g., bispecific antibodies), antibody fragments, immunoadhesins and antibody-immunoadhesin chimerias.

An "antibody fragment" includes at least a portion of a full length antibody and typically an antigen binding or variable region thereof. Examples of antibody fragments include Fab, Fab', F(ab')$_2$, and Fv fragments; single-chain antibody molecules; diabodies; linear antibodies; and multispecific antibodies formed from engineered antibody fragments.

The term "monoclonal antibody" is used in the conventional sense to refer to an antibody obtained from a population of substantially homogeneous antibodies such that the individual antibodies comprising the population are identical except for possible naturally occurring mutations that may be present in minor amounts. Monoclonal antibodies are highly specific, being directed against a single antigenic site. This is in contrast with polyclonal antibody preparations which typically include varied antibodies directed against different determinants (epitopes) of an antigen, whereas monoclonal antibodies are directed against a single determinant on the antigen. The term "monoclonal", in describing antibodies, indicates the character of the antibody as being obtained from a substantially homogeneous population of antibodies, and is not to be construed as requiring production of the antibody by any particular method. For example, monoclonal antibodies used in the present invention can be produced using conventional hybridoma technology first described by Kohler et al., Nature 256:495 (1975), or they can be made using recombinant DNA methods (see, e.g., U.S. Pat. No. 4,816,567). Monoclonal antibodies can also be isolated from phage antibody libraries, e.g., using the techniques described in Clackson et al., Nature 352:624-628 (1991); Marks et al., J. Mol. Biol. 222:581-597 (1991); and U.S. Pat. Nos. 5,223,409; 5,403,484; 5,571,698; 5,427,908 5,580,717; 5,969,108; 6,172,197; 5,885,793; 6,521,404; 6,544,731; 6,555,313; 6,582,915; and 6,593,081).

The monoclonal antibodies described herein include "chimeric" and "humanized" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). "Humanized" forms of non-human (e.g., murine) antibodies are chimeric antibodies which contain minimal sequence derived from non-human immunoglobulin. For the most part, humanized antibodies are human immunoglobulins (recipient antibody) in which the hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

Chimeric or humanized antibodies can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

The monoclonal antibodies described herein also include "human" antibodies, which can be isolated from various sources, including, e.g., from the blood of a human patient or recombinantly prepared using transgenic animals. Examples of such transgenic animals include KM-MOUSE® (Medarex, Inc., Princeton, N.J.) which has a human heavy chain transgene and a human light chain transchromosome (see WO 02/43478), XENOMOUSE® (Abgenix, Inc., Fremont Calif.; described in, e.g., U.S. Pat. Nos. 5,939,598; 6,075,181; 6,114,598; 6, 150,584 and 6,162, 963 to Kucherlapati et al.), and HUMAB-MOUSE® (Medarex, Inc.; described in, e.g., Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, U.S. Pat. Nos. 5,545,806; 5,569,825; 5,625,126; 5,633,425; 5,789,650; 5,877,397; 5,661,016; 5,814,318; 5,874,299; and 5,770,429; 5,545,807; and PCT Publication Nos. WO 92/03918, WO 93/12227, WO 94/25585, WO 97/13852, WO 98/24884 and WO 99/45962, WO 01/14424 to Korman et al.). Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

III. Mixtures Containing a Protein of Interest

The methods of the invention can be applied to any mixture containing a protein of interest. In one embodiment, the mixture is obtained from or produced by living cells that express the protein to be purified (e.g., naturally or by genetic engineering). Optionally, the cells in a cell culture include cells transfected with an expression construct containing a nucleic acid that encodes a protein of interest. Methods of genetically engineering cells to produce proteins are well known in the art. See e.g., Ausubel et al., eds. (1990), Current Protocols in Molecular Biology (Wiley, New York) and U.S. Pat. Nos. 5,534,615 and 4,816,567, each of which are specifically incorporated herein by reference. Such methods include introducing nucleic acids that encode and allow expression of the protein into living host cells. These host cells can be bacterial cells, fungal cells, insect cells or, preferably, animal cells grown in culture. Bacterial host cells include, but are not limited to *E. coli* cells. Examples of suitable *E. coli* strains include: HB101, DH5α, GM2929, JM109, KW251, NM538, NM539, and any *E. coli* strain that fails to cleave foreign DNA. Fungal host cells that can be used include, but are not limited to, *Saccharomyces cerevisiae, Pichia pastoris* and *Aspergillus* cells. Insect cells that can be used include, but are not limited to, *Bombyx mori, Mamestra drassicae, Spodoptera frugiperda, Trichoplusia ni, Drosophilia melanogaster.*

A number of mammalian cell lines are suitable host cells for expression of proteins of interest. Mammalian host cell lines include, for example, COS, PER.C6, TM4, VERO076, DXB11, MDCK, BRL-3A, W138, Hep G2, MMT, MRC 5, FS4, CHO, 293T, A431, 3T3, CV-1, C3H10T1/2, Colo205, 293, HeLa, L cells, BHK, HL-60, FRhL-2, U937, HaK, Jurkat cells, Rat2, BaF3, 32D, FDCP-1, PC12, M1x, murine myelomas (e.g., SP2/0 and NS0) and C2C12 cells, as well as transformed primate cell lines, hybridomas, normal diploid cells, and cell strains derived from in vitro culture of primary tissue and primary explants. New animal cell lines can be established using methods well known by those skilled in the art (e.g., by transformation, viral infection, and/or selection). Any eukaryotic cell that is capable of expressing the protein of interest may be used in the disclosed cell culture methods. Numerous cell lines are available from commercial sources such as the American Type Culture Collection (ATCC®). In one embodiment of the invention, the cell culture, e.g., the large-scale cell culture, employs hybridoma cells. The construction of antibody-producing hybridoma cells is well known in the art. In one embodiment of the invention, the cell culture, e.g., the large-scale cell culture, employs CHO cells to produce the protein of interest such as an antibody (see, e.g., WO 94/11026). Various types of CHO cells are known in the art, e.g., CHO-K1, CHO-DG44, CHO-DXB11, CHO/dhfr$^-$ and CHO-S.

In certain embodiments, the present invention contemplates, prior to purifying a protein of interest from a cell culture, monitoring particular conditions of the growing cell culture. Monitoring cell culture conditions allows for determining whether the cell culture is producing the protein of interest at adequate levels. For example, small aliquots of the culture are periodically removed for analysis in order to monitor certain cell culture conditions. Cell culture conditions to be monitored include, but not limited to, temperature, pH, cell density, cell viability, integrated viable cell density, lactate levels, ammonium levels, osmolality, and titer of the expressed protein. Numerous techniques are well known to those of skill in the art for measuring such conditions/criteria. For example, cell density may be measured using a hemocytometer, an automated cell-counting device (e.g., a COULTER COUNTER®, Beckman Coulter Inc., Fullerton, Calif.), or cell-density examination (e.g., CEDEX®, Innovatis, Malvern, Pa.). Viable cell density may be determined by staining a culture sample with Trypan blue. Lactate and ammonium levels may be measured, e.g., with the BIOPROFILE® 400 Chemistry Analyzer (Nova Biomedical, Waltham, Mass.), which takes real-time, online measurements of key nutrients, metabolites, and gases in cell culture media. Osmolality of the cell culture may be measured by, e.g., a freezing point osmometer. HPLC can be used to determine, e.g., the levels of lactate, ammonium, or the expressed protein. In one embodiment of the invention, the levels of expressed protein can be determined by using, e.g., protein A HPLC. Alternatively, the level of the expressed protein can be determined by standard techniques such as Coomassie staining of SDS-PAGE gels, Western blotting, Bradford assays, Lowry assays, biuret assays, and UV absorbance. Optionally, the present invention may include monitoring the post-translational modifications of the expressed protein, including phosphorylation and glycosylation.

In a specific embodiment, methods of the present invention comprise effectively removing contaminants from a mixture (e.g., a cell culture, cell lysate or clarified bulk) which contains a high concentration of a protein of interest (e.g., an antibody). For example, the concentration of a protein of interest may range from about 0.5 to about 50 mg/ml (e.g., 0.5, 1, 5, 10, 15, 20, 25, 30, 35, 40, 45 or 50 mg/ml).

Preparation of mixtures initially depends on the manner of expression of the protein. Some cell systems directly secrete the protein (e.g., an antibody) from the cell into the surrounding growth media, while other systems retain the antibody intracellularly. For proteins produced intracellularly, the cell can be disrupted using any of a variety of methods, such as mechanical shear, osmotic shock, and enzymatic treatment. The disruption releases the entire contents of the cell into the homogenate, and in addition produces subcellular fragments which can be removed by centrifugation or by filtration. A similar problem arises, although to a lesser extent, with directly secreted proteins due to the natural death of cells and release of intracellular host cell proteins during the course of the protein production run.

In one embodiment, cells or cellular debris are removed from the mixture, for example, to prepare clarified bulk. The methods of the invention can employ any suitable methodology to remove cells or cellular debris. If the protein is produced intracellularly, as a first step, the particulate debris, either host cells or lysed fragments, can be removed, for example, by a centrifugation or filtration step in order to prepare a mixture which is then subjected to purification according the methods described herein (i.e., from which a protein of interest is purified). If the protein is secreted into the medium, the recombinant host cells may be separated from the cell culture medium by, e.g., centrifugation, tangential flow filtration or depth filtration, in order to prepare a mixture from which a protein of interest is purified.

In another embodiment, cell culture or cell lysate is used directly without first removing the host cells. Indeed, the methods of the invention are particularly well suited to using mixtures comprising a secreted protein and a suspension of host cells.

IV. Contaminants Precipitation by Caprylic Acid

According to the present invention, removal of contaminants from a mixture that has been "partially purified" by a first chromatography step (e.g., an affinity chromatography) is achieved by precipitation with caprylic acid. In a specific embodiment, the elution solution collected from the first chromatography step is precipitated by caprylic acid.

The concentration of caprylic acid sufficient to precipitate contaminants from a particular mixture can be determined empirically for each protein mixture using methods described herein. The final concentration of caprylic acid added to the mixture is at least 0.05% volume/volume (v/v), for example between about 0.05% and 20% (v/v), preferably between about 0.5% and 1% (v/v).

In certain embodiments, the pH of the mixture is altered to facilitate precipitation. The optimum pH required to facilitate caprylic acid precipitation of a particular contaminant can be determined empirically for each protein mixture using methods described herein. Preferably the final pH of the mixture is altered to be between about 3 and 7 (e.g., about 3, 4, 5, 6, or 7). In a particular embodiment, the pH of the mixture is altered to be from about 5 to 6 (e.g., 5.1, 5.2, 5.3, 5.4, 5.5, 5.6, 5.7, 5.8, 5.9 or 6.0). The pH of the mixture can be adjusted before or after the addition of caprylic acid to the mixture. In a preferred embodiment, the pH of the mixture is adjusted before the addition of caprylic acid. In general, any art recognized acids or buffers can be used to alter the pH of a mixture, including, for example, acetate- and citrate-containing buffers. An advantage of using a bioreactor cell culture is that the pH of the cell culture medium can be monitored and adjusted by addition of one or more suitable acids or buffers to the cell culture medium in the bioreactor.

In certain embodiments, the caprylic acid is added to the mixture and mixed for a particular length of time prior to removing the contaminant precipitate. The optimum length of mixing required to facilitate caprylic acid precipitation of a particular contaminant can be determined empirically for each protein mixture using methods described herein. Preferably the mixing time is greater than about 5 minutes (e.g., about 5, 10, 15, 20, 30, 60, 90, 120, 240, or 480 minutes). In a particular embodiment, the mixing time is about 60 minutes.

The present disclosure is further illustrated by the following examples, which should not be construed as further limiting. The contents of all figures and all references, patents and published patent applications cited throughout this application are expressly incorporated herein by reference in their entireties.

Example 1

Introduction

Monoclonal antibody (mAb) purification processes exist in different well-established platforms with extensive process performance histories from both commercial and clinical mAb production [1-4]. These industrial purification process platforms typically use three chromatographic steps—a Protein A chromatography capture step followed by two polishing chromatography steps. The polishing steps consist of ion exchange, hydrophobic interaction, or mixed mode chromatography columns [1-4]. The rapidly growing demands for therapeutic antibody production and the increasing mammalian cell culture titers induce manufacturing facility challenges including larger chromatography column and buffer tank size constraints. High-binding capacity resins may help to reduce column size and buffer usage. However, resins are expensive.

To continuously improve the speed and ease of processing and minimize cost while maintaining the level of purity and quality of the product, it is essential to develop an alternative purification method which can replace one chromatography step and overcome the potential capacity constraints on a facility. Precipitation-based purification technologies have the potential to remove impurities at higher protein concentration, allowing higher antibody titer cell culture broth (CB) to be processed with the same equipment [5-18]. By replacing a polishing chromatography step with a precipitation technology, it is possible to alleviate some facility fit constraints and could reduce processing time under more competitive cost.

Industrial precipitation methods include ethanol precipitation [17, 18], ammonium sulfate [9, 11, 13, 15], Cohn fractionation [12], or polyethylene glycol precipitation [5, 10, 16], and caprylic acid (CA) precipitation [6, 7, 12, 14, 19]. CA is an eight-carbon saturated fatty acid which is found naturally in the milk of various mammals, and as a minor constituent of coconut oil and palm kernel oil. The administration of large volumes of albumin containing 4-20 mM CA over a 50-year period suggested that CA at the administrated concentration showed nontoxic effects [20, 21]. The injection of caprylate into the mice at moderate levels (600 mg/kg mice body weight) showed no-toxic [22]. CA has been used as precipitating agent for cell debris, impurities, and viruses during the harvest step post protein fermentation [6, 7, 14]. This method involves selective precipitation of impurities while maintaining the protein of interest in solution. In this study, CA precipitation was evaluated as an alternative purification method post protein A affinity purification step to replace a polishing chromatography step for developing a two-chromatography step mAb purification process, as shown in FIG. 1. One benefit to this approach is that the precipitation operation can be performed just after low pH viral inactivation (VI) step in the same container without additional operational step and material transfer. The precipitated impurities were then removed from the process stream by filtration to minimize product loss. The effects of pH, CA concentrations, mAb concentrations, buffer systems, operational temperatures, and mixing time on the impurity removal, product recovery, and purity were investigated. The step yield and the levels of HCPs and high-molecular weight (HMW) species were monitored.

Materials and Methods

Materials

MabSelect Protein A resin was purchased from GE Healthcare (Uppsala, Sweden). CA from Amresco (Solon, Ohio) was used for all precipitation studies. The reverse phase high-performance liquid chromatography (HPLC) column (Jupiter 5 U C18 250×4.60 mm RP column) for residual CA determination was obtained from PHENOMENEX® (Torrance, Calif.). The pre-packed cation exchange chromatography (CEX) column (POROS® XS, 1.2 cm×5 cm) was obtained from Life Technology (Grand Island, N.Y.). 3M ZETA PLUS® VR filters were from 3 M Purification Inc. (Meriden, Conn.). The mAbs in this study were expressed by various genetically engineered Chinese Hamster Ovary (CHO) cells and produced at Bristol-Myers Squibb in the United States.

Equipment

All preparative chromatography experiments were carried out on an AKTA Avant chromatography system from GE Healthcare (Uppsala, Sweden) with built-in UV, pH and conductivity detectors to monitor the effluent and fraction collectors with temperature control to collect the fractions from the chromatographic experiments.

Methods

Protein A Chromatography Capture Step.

MabSelect (GE Healthcare, Uppsala, Sweden) Protein A column was used to capture antibody from the clarified cell CB. The MabSelect chromatography purification has been well described in previous publication [23]. The purification was operated at a resin retention time of 3-10 min. The chromatography columns were equilibrated with phosphate buffered saline (PBS), pH 7.4 buffer. The clarified product bulk was then loaded onto the MabSelect column at a loading capacity of approximately 40 mg/mL resin. After loading, the column was washed with PBS and an intermediate pH buffer to remove loosely bound host-cell proteins (HCPs) and media components and the antibody was eluted from the column using a low pH buffer (pH 2.5-4.0). The effluent during the elution phase was collected and analyzed for protein concentration, HCPs, DNA, and aggregates. The MabSelect elution pools were then used for the CA-induced impurity precipitation studies.

Caprylic Acid Induced Impurity Precipitation:

Impurity precipitation was initiated by adding CA solution into the protein A elution pool at the concentration of 0-1% CA (volume/volume, v/v) solution. The mixtures were stirred greater than 15 min at ambient temperature and the pH of the mixture was adjusted to different pHs between 4.5 and 7.0 according to the study design. The impurity precipitation conditions were then optimized with a full factorial design of experiment (DoE) at a 10-mL protein A elution pool scale. After CA treatment, the precipitation was removed by filtration through a Pall ACRODISC® PF Syringe filter (0.8/0.2-μm polyether sulfone membrane filter, Pall, Port Washington, N.Y.) or CORNING® 0.2-μm cellulose acetate membrane cup filter (13.6 $cm^2$) for small scale and Millistake depth filter (MCOHC, 23 $cm^2$, 0.2-0.8 μm pore size, EMD Millipore, Billerica, Mass.) or 3 M ZETA PLUS® VR Series Depth Filter (BC0025LVR07, 25 $cm^2$, 0.2-0.8 μm pore size, 3 M Purification Inc., Meriden, Conn.) for large scale. The filtrate was collected as the product stream for further purification process and product quality analysis. The capacities of the prewetted depth filters with an area of 25 $cm^2$ were evaluated to a final pressure drop of 20 psig. For experiments in which a pressure drop of 20 psig was not reached, the achieved throughputs and related pressure drops were reported.

Ion Exchange Chromatography Polishing Step:

CEX step was evaluated as the polishing chromatography step post CA-based impurity precipitation in the two-chromatography-step process. Prepacked POROS® XS CEX column (1.2 cm×5 cm=5.7 mL; Thermo Fisher Scientific-Life Technology, Inc., Grand Island, N.Y.) was operated in bind and elute mode. The column was equilibrated with a buffer at pH 5.0. Following equilibration, the clarified CA precipitation product pool containing residual CA was loaded onto the CEX column and bound. The column was then washed with equilibration buffer and wash buffer at pH 6.2. The antibody was eluted from the CEX column with elution buffer.

Analytical Methods

HPLC-Protein A Titer:

Antibody concentration in various product pools were determined by HPLC-protein A affinity chromatography using the POROS® A/20 protein A affinity column, 2.1×30 mm (Thermo Fisher Scientific-Life Technologies, Grand Island, N.Y.). The separation was carried out at 2.0 mL/min. The sample injection volume is from 10 to 100 μL (approximately 10-50 μg) if the estimated protein concentration is ~0.1-5.0 mg/mL to ensure the injected mAb in the sample to be completely captured by the column. The calibration curve was made using each individual purified mAb (>99% purity). The antibody binds to the Protein A column under neutral buffer conditions (pH 7.4) and is eluted under acidic conditions (pH 2.6). The area of the antibody peak is directly proportional to the antibody concentration. Unknown antibody concentrations can be determined from a calibration curve created using reference antibody materials. The accuracy of this mAb concentration measurement is ±10%.

Host Cell Protein (HCP) Analysis:

HCPs levels were determined by an enzyme-linked immunosorbent assay (ELISA) method using CHO HCP third Generation kit (Immunoenzymetric Assay for the measurement of CHO HCPs, Cygnus Technologies, Southport, N.C.). Prior to the analysis, samples were diluted using the sample dilution buffer (Cygnus Technologies, Southport, N.C.). The ELISA procedure followed manufacturer protocol. Absorbance was measured at 450/650 nm, blanking on the 0 ng/mL standard. The quantification limit of HCP assay is 1.0 ng/mL. The accuracy of HCP—ELISA assay is ±30%.

Size Exclusion Chromatography:

HMW and the purity of the product samples were quantified by analytical SEC with a TSK gel G3000SW column (7.5 mm ID×30 cm, 10 μm average particle size, Tosoh Bioscience, Japan) using a Waters system (2695 separation module and 2996 Photodiode Array Detector, MA, USA). PBS at pH 6.8 was used as the mobile phase at a flow rate of 1 mL/min. The injection amount is 100 μg proteins. The accuracy of monomer % in SEC—HPLC is ±2%.

Host Cell DNA by qPCR:

The method for host cell DNA quantification is designed to quantitate CHO genomic DNA by quantitative Polymerase Chain Reaction (qPCR). The qPCR assay is performed using a fluorogenic probe and flanking forward and reverse primers designed to bind to a repetitive sequence within the CHO genome. The samples are diluted, purified by Wako kit (VA), and combined with a PCR master mix. Successive cycles of template denaturation, primer annealing, and product extension are used to amplify the target sequence. During the extension step of the amplification cycles, the reporter dye is released from the probe and is detected as a fluorescent signal. The samples and standards, along with PCR master mix-containing primers and probe, were then loaded in 96-well plate format onto Applied Biosystem 7900HT Sequence Detection System (Thermo Fisher Scientific-Life Technology, Grand Island, N.Y.), where the DNA was quantified using real-time PCR. The quantification limit of DNA is 1.0 pg/mL. The accuracy of residual DNA measurement is ±5%.

Residual Caprylic Acid:

Residual CA in the samples was analyzed by a reverse phase-HPLC (RP-HPLC) method. The CA in the sample was extracted from protein solution by precipitating proteins using acetonitrile and removing of precipitated proteins by centrifugation. The recovered supernatant is then separated by reverse phase HPLC chromatography system equipped with an UV detector using a PHENOMENEX® Jupiter 5 U C18 250 mm×4.60 mm RP column. The separation is obtained with the mixture of water, acetonitrile, and trifluoroacetic acid and as a mobile phase. The CA is detected at 215 nm as it is eluted from the column. The area of the CA peak is directly proportional to the CA concentration. Unknown concentrations can be determined from a calibration curve created using CA as reference material. The quantification limit of CA in sample is 0.2 mg/mL. The accuracy of residual CA measurement is ±10%.

Binding ELISA Analysis:

The relative binding activity of mAb was determined using an ELISA method. Briefly, a microtiter plate is coated with recombinant protein (antigen) and blocked with a bovine serum albumin buffer. The mAb sample is added onto the microtiter plate with coated recombinant protein and the recombinant protein (antigen) on the coated plate captures the mAb in the sample. Subsequently a goat anti-human IgG (Fc Specific) conjugated with HRP is added which binds to the mAb. The addition of a substrate reacts with HRP producing color. The amount of color produced is directly proportional to the amount of mAb in the sample. The relative binding activity of mAb is calculated using parallel line analysis as relative to concurrently analyzed reference material. The specification of the relative binding activity of mAb to the reference material by ELISA method is 50-150%.

Results and Discussion

Development of Optimal Conditions for Caprylic Acid-Induced Impurity Precipitation To develop a two-chromatography purification process, a quality by design (QbD) risk assessment approach has been implemented for the study design. The QbD risk assessment approach begins with predefined objectives and emphasizes product and process understanding and process control, all based on sound science and quality risk management. Based on risk assessment by evaluating the historical data in Bristol-Myers Squibb, one potential step-viral inactivation/neutralization (VIN) step post protein A column purification, as shown in FIG. 1, was identified for further improvement to enable a two-chromatography purification process (one protein A affinity capture column step and one polishing chromatography step). Product quality should not be compromised and additional equipments and/or facility changes need to be minimized. Three major impurities, HCPs, aggregates, and virus, were identified as having moderate and above-risk if one of the polishing column steps was removed from original three-chromatography-step purification process without adding other purification method.

Industrial scale precipitation is possible using existing bioprocessing equipment and disposable technology. Precipitation can effectively reduce HCP, product-related impurities, and virus [5-19, 24]. Precipitation methods have been widely used in purifying proteins from blood material, ascites fluid, and egg white in combination with column chromatography [8, 9, 11-13, 17-19, 24]. They are often designed to precipitate the protein of interest while leaving impurities in solution. One benefit to this approach is the reduction in pool volume by minimizing the volume used to resolubilize the precipitate. This method has a disadvantage for manufacturing production due to the need to capture the precipitate.

CA has been used to precipitate impurities, such as HCPs and leave the product (antibodies) in solution [6-8, 12, 14, 19]. CA is commonly used to precipitate cell debris, albumin, and other non-IgG proteins from serum and ascites fluid to purify immunoglobulins [12, 14]. A different approach used in this study is to precipitate impurities from the Protein A column elution pool while leaving the antibody in the solution. The advantage of conducting precipitation in Protein A elution pool is to minimize product loss and maximize impurity clearance with a relatively pure product stream. Furthermore, the product volume is relative low and it is easy to operate with the existing equipment.

Figure 2A:
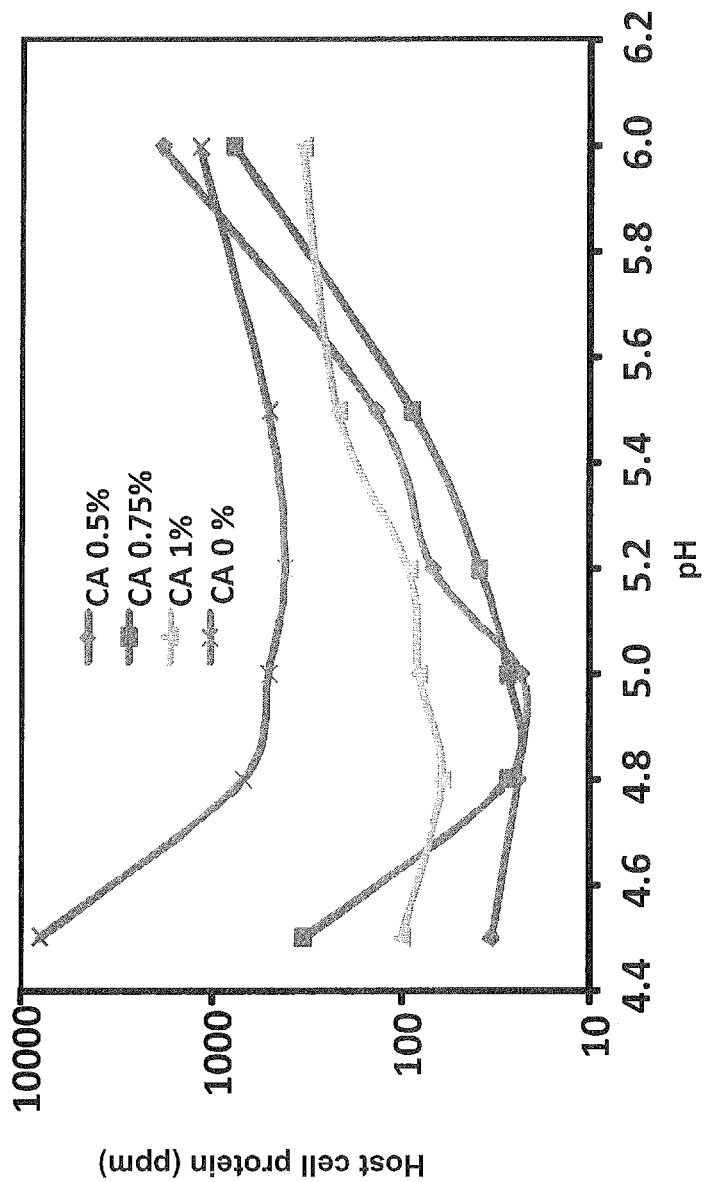
FIG. 2 shows effect of caprylic acid (CA) concentration on the HCP and HMW impurity reduction and step yield at pH range of 4.5-6.0. CA was added and the samples were mixed at ambient temperature for approximately 60 min and then the solution was filtered using CORNING® 0.2-μm sterile filter. Control samples were pH adjusted, sterile filtered, and analyzed without addition of CA. (a) HCP reduction as functions of pH and CA concentrations. (b) The percent monomer in SEC as functions of pH and CA concentrations, and (c) the step yield as functions of pH and CA concentrations. For CA precipitation, the estimated measurement error is less than 10%. For assay accuracy, HCPs is ±30%; mAb concentration by Protein A-HPLC is ±10%; monomer % by SEC is ±2%.
Figure 2B:
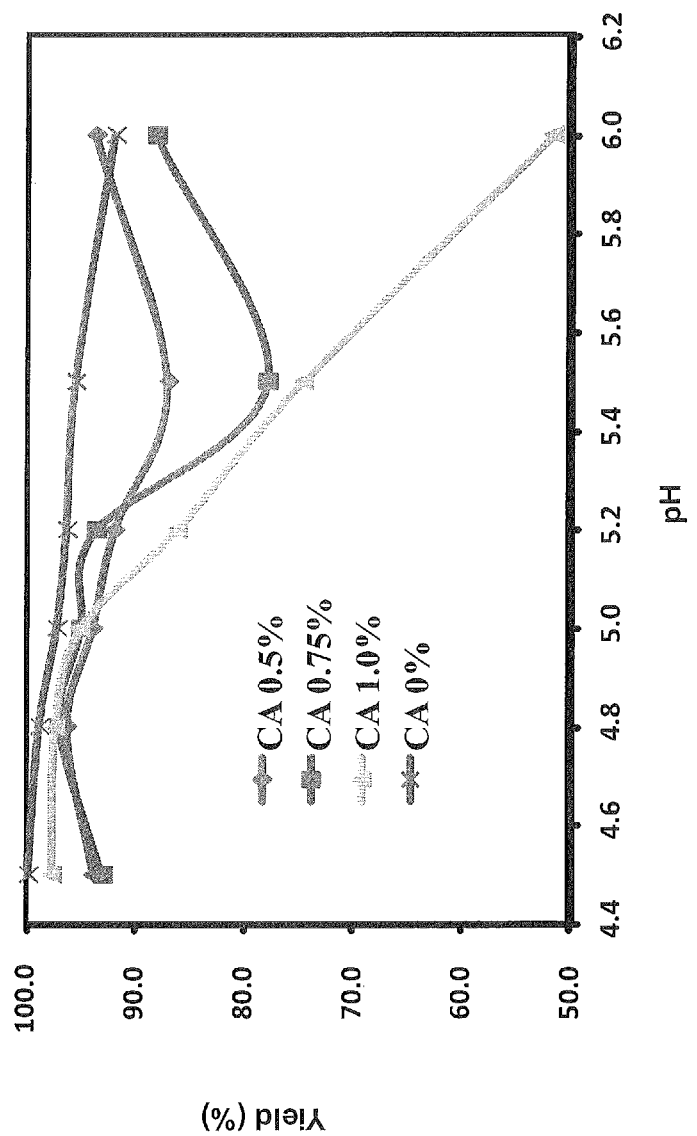
Figure 2C:
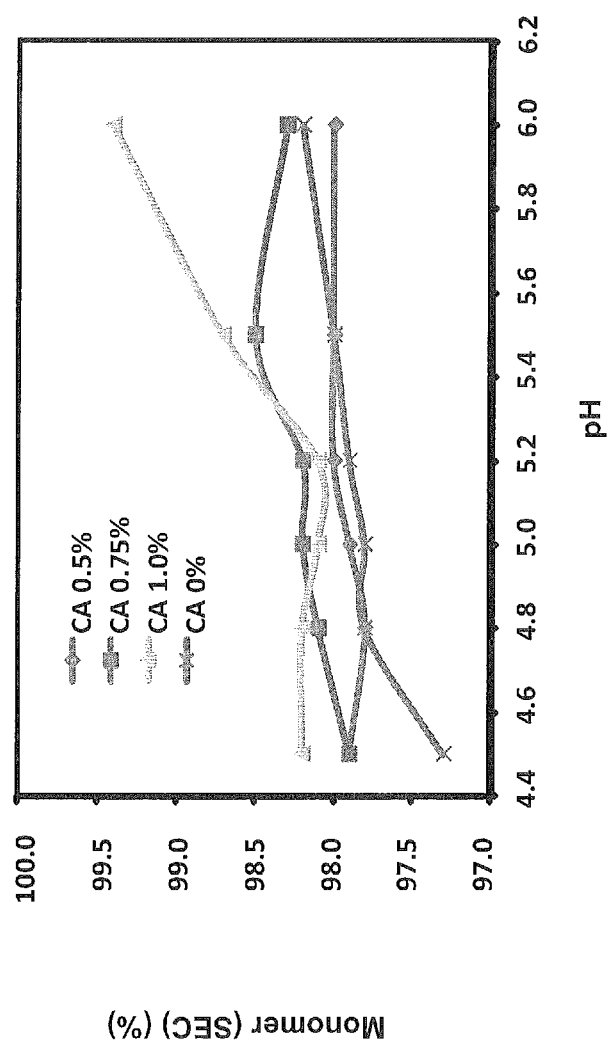

Five mAbs (three IgG1 and two IgG4) outlined in Table 1 were selected to test CA-based impurity precipitation from the protein A column elution pool. Applicants initially studied the effect of pH on the HCP removal in protein A column elution pool of an IgG1 (mAb I) with pI of approximately 8.8. In the pH range of 4.5-6.0 studies (FIG. 2a), it was found that pH<4.5 was not effective in precipitating HCPs and adverse effect on HCP clearance was observed while pH was >6.0. The optimal pH range is between 4.8 and 5.8. Within the optimal pH (4.8-5.8), HCP $\log_{10}$ reduction value (LRV) can approximately be 1.27 LRVs at maximum, indicating changing pH alone cannot sufficiently remove the HCPs to an acceptable level. Further HCP reduction was observed by adding CA in the protein A column elution. The effect of CA concentration on HCP removal was tested in the CA concentration of 0.5-1% (v/v) at the pH 4.5-6.0 range. Using CA as a precipitation agent at the optimal pH range, HCPs can be significantly reduced to below 100 ppm (FIG. 2a). Approximately 20 ppm HCPs level (2.47 LRVs) was achieved by adding approximately 0.5-0.75% (v/v) CA. Besides HCPs, mAb purity, residual DNA level and step yield were also monitored. At all three CA concentrations (0.5, 0.75, and 1%) showed a comparable yield and aggregate removal (FIG. 2b,c). At 0.75% (v/v) of CA concentration at pH 5.2, the percent monomer in SEC was 98.2%, comparable with that without CA (~97.9%; FIG. 2c). The step yield is approximately 94% at pH 5.2, which is comparable to that without addition of CA (FIG. 2b). The lower yields at pH 5.5 for CA<0.75% shown in FIG. 2b could be due to coprecipitation of mAb with HCPs and CA. DNA levels in the CA precipitation product pool were undetectable for all of tested conditions (the quantification limit of DNA is 1 pg/mL). Since near complete clearance of DNA was observed for the CA precipitation product pool, it was excluded from the testing in the subsequent condition optimization.

TABLE 1

A List of Monoclonal Antibodies Used for Caprylic Acid Precipitation Studies

| Monoclonal antibody | Subtype | pI range |
| --- | --- | --- |
| Mab I | IgG1 | 7.5-9.0 |
| Mab II | IgG1 | 7.5-8.5 |
| Mab III | IgG4 | 7.0-8.5 |
| Mab IV | IgG4 | 6.5-7.5 |
| Mab V | IgG1 | 7.0-8.5 |

Figure 3:
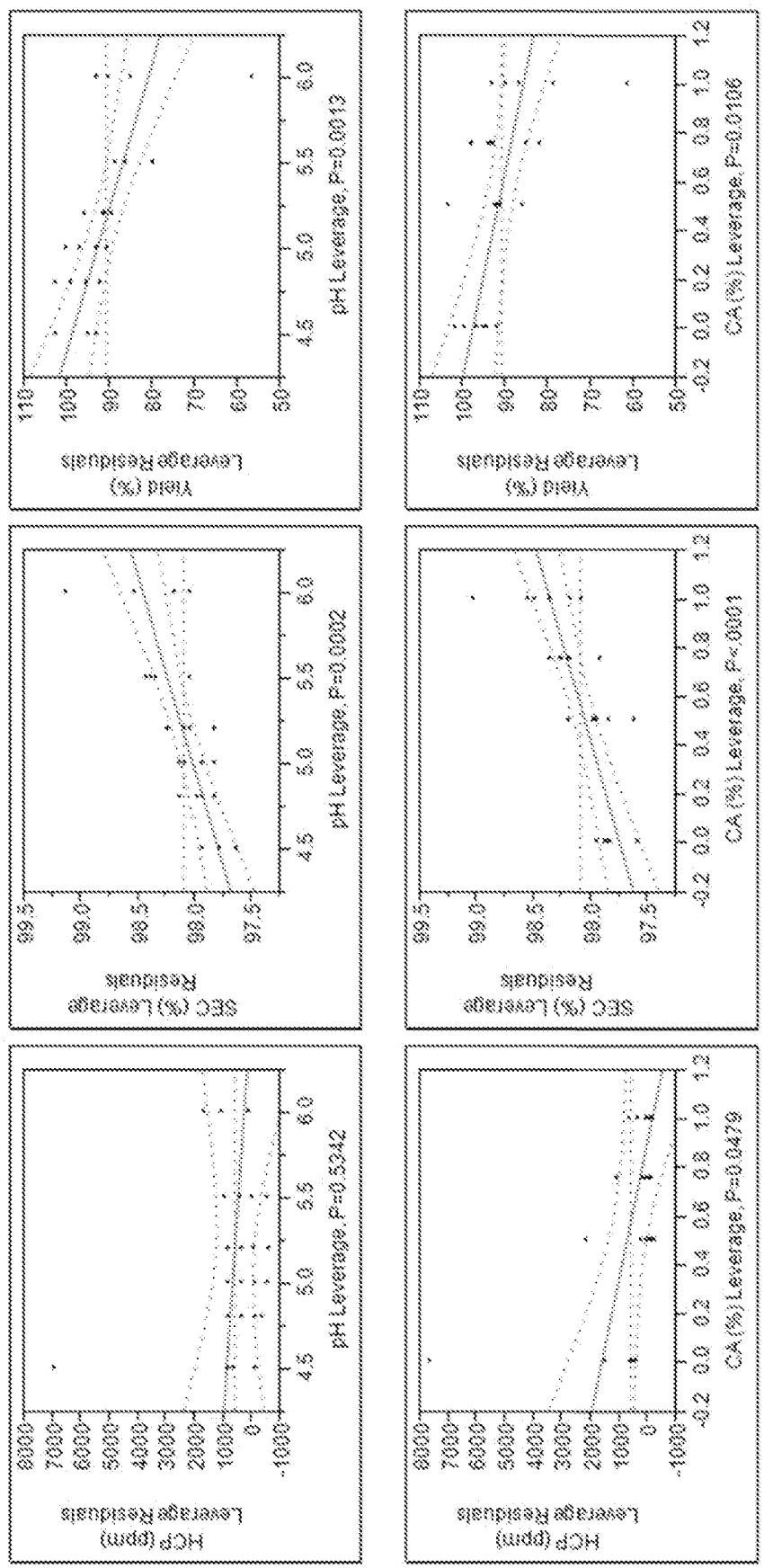
FIG. 3 shows mAb I Protein A elution pool CA-induced precipitation DoE main effects plots testing effects of pH and CA concentration. A DoE was performed testing the effects of varying CA concentrations and pHs simultaneously. The pH range tested was from 4.5 to 6.0. The CA concentration range tested was 0-1% (v/v). The main effects plots independently display the effect of CA concentration and pH on the aggregates (percent monomer in SEC), yield and HCP levels.
Figure 4:
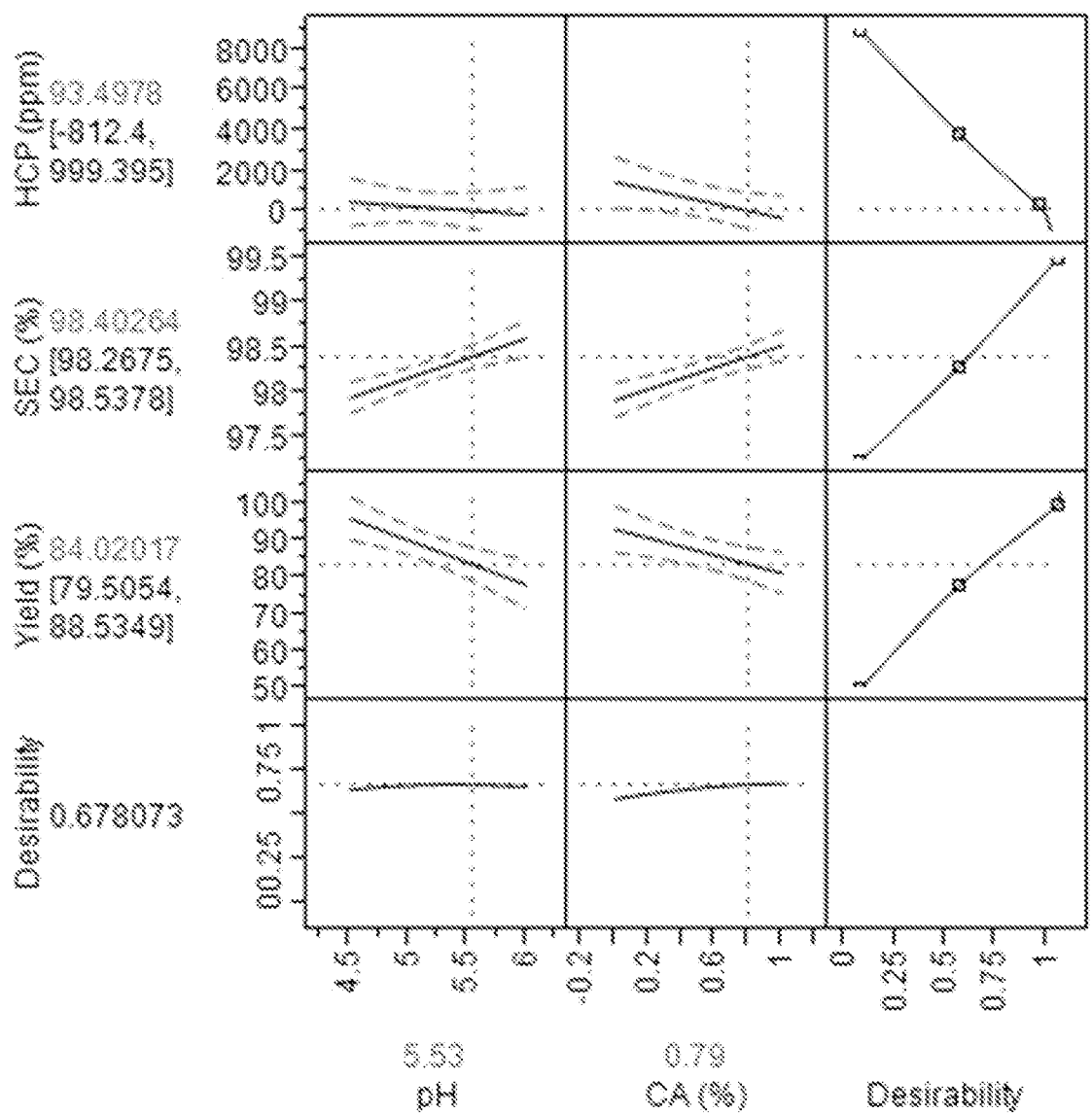
FIG. 4 shows prediction profiles for CA-induced impurity precipitation process robustness study. Step yield, HCP level, and percent monomer in SEC were analyzed as a function of pH and CA concentration. The blue lines represent the confidence intervals of prediction profiles.

In order to test the robustness of CA precipitation, a DoE study was performed with mAb I. The DoE study allowed us to determine which parameters had the largest effects and to identify interactions among the different precipitation parameters. CA concentration and pH of the protein A elution pool were changed simultaneously in a full factorial experiment. The DoE study results were used to develop the pH and CA concentration response models for HCPs level, the percent monomer (SEC-HPLC) and yield of the product pools. As shown in the regression plots (FIG. 3), the response model is curved over the ranges tested for pH and CA concentration and the CA concentration leverage plot shows an downward trend in the HCPs level response as the CA concentration increases (P<0.05). Increasing the CA concentration decreases the HCPs concentration in the product pool. Although pH shows slight effect on the HCPs concentration, there is no statistically significant effect on HCPs reduction (P>0.05). Both pH and CA concentrations affect the aggregates (the percent monomer in SEC) and yield. Increasing the pH and CA concentrations increase percent monomer in SEC, indicating CA precipitation in combination with pH adjustment is able to remove some aggregates. The yield of the antibody was high in the solution. Therefore, CA precipitation has a good selectivity and efficiency. Selective precipitation of HCPs and aggregates was seen where precipitated HMWs and HCPs were removed by sterile filtration but the mAb of interest remained in solution. The optimal precipitation condition is a balance of acceptable yield, low HCPs, and high-percent monomer levels. In this case, the conditions of pH 5.5 with CA concentration of 0.79% (v/v), provides the best results with HCPs at approximately <93 ppm, monomer >98.4%, and yield of >84%, as shown in FIG. 4.

Industrial bioprocessing often requires extended processing hold times and variable storage conditions. To evaluate the suitability of CA precipitation for large scale manufacturing, Applicants studied the impact of incubation at common operating and storage temperatures. As shown in Table 2, lower temperature (5° C.) is less effective on HCPs removal. The HCPs level at 15° C. is comparable with that at 25° C. The HCPs level in the control experiment without CA at 25° C. is 442 ppm, much higher than that with 0.75% CA (19 ppm). Yields and the percent monomer (SEC-HPLC) are also consistent at temperature from 15 to 25° C., which are comparable with the control experiment without CA at 25° C. The results indicate that CA precipitation step is robust from 15° C. to ambient temperature.

TABLE 2

Effect of Temperature on HCP, Aggregates (SEC) and Yield Levels for Caprylic Acid Precipitation Process

| | With 0.75% caprylic acid | | | Without 0.75% caprylic acid | | |
|---|---|---|---|---|---|---|
| | Incubation Temperature | | | | | |
| | 5° C. | 15° C. | 25° C. | 5° C. | 15° C. | 25° C. |
| HCPs (ng/mg) (ppm) | 226 | 27 | 19 | | | |
| SEC (monomer %) | 99.5 | 99.3 | 99.4 | | | |
| Yield (%) | >99.0 | >99.0 | 97.0 | 94.4 | 94.0 | 96.4 |

The mAb used in this study is mAb II. The HCPs in Protein A column elution pool is 616 ppm. All experiments were performed at pH 5.5 with or without 0.75% CA.

Figure 5:
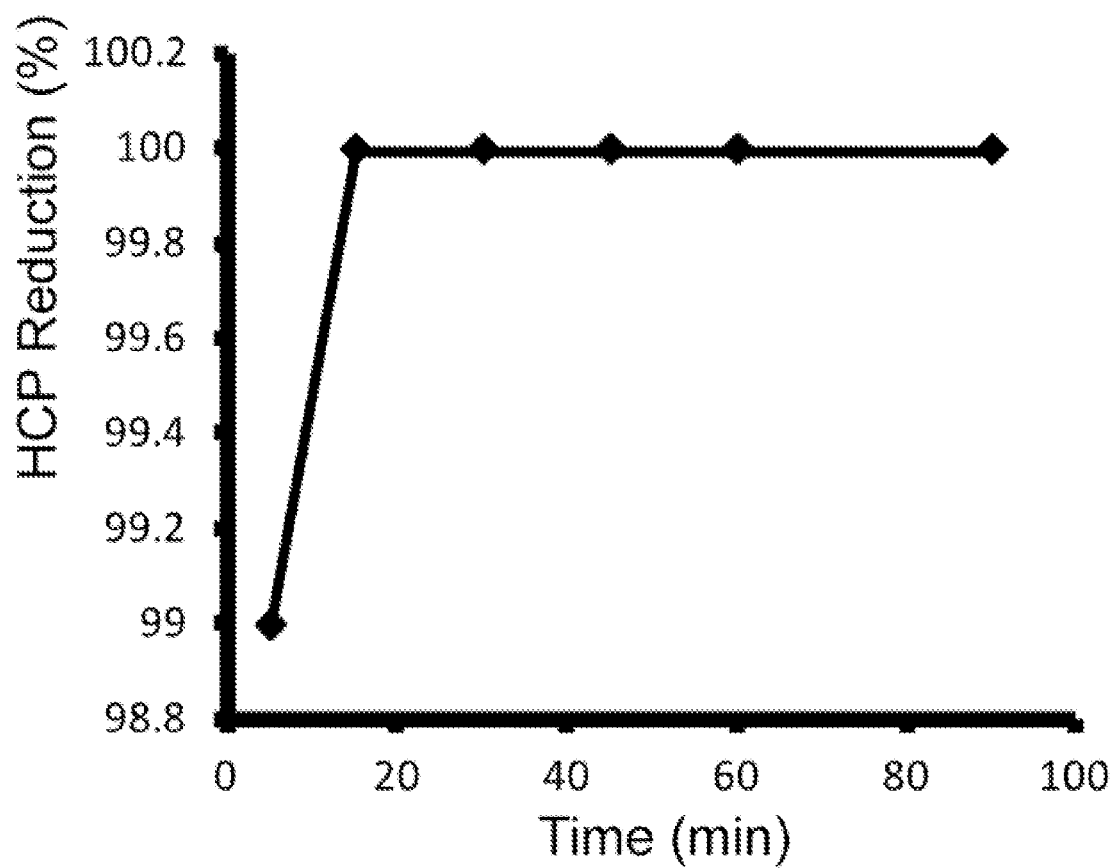
FIG. 5 shows effect of mixing time on HCP reduction at pH 5.5 with 0.75% CA.

The effect of mixing time on the CA precipitation for HCP clearance was also investigated. Post addition of CA into protein A elution pool with pH adjustment, the mixture was stirred at ambient temperature up to 90 min. The sample was taken every 15 min and filtered. HCPs in the filtered product pool were analyzed and the results were shown in FIG. 5. The results indicate that the HCP level decreases to <10 ppm at very short period of time (few minutes) and reaches plateau.

Antibody concentrations and buffer systems did not impact precipitation performance, as shown in Table 3. No differences in impurity reduction or yield were observed between the different buffer systems (as shown in Table 3). The impact of process variables on CA precipitation of impurities was the same in different buffer systems.

Product yield, percent monomer (% SEC) and HCP reduction are stable for all of tested monoclonal antibody concentrations and two buffer systems (Table 3).

TABLE 3

Effects of Monoclonal Antibody Concentration and Buffer on HCP, Aggregates (SEC) and Yield Levels for Caprylic Acid Precipitation Process

| Mab Concentration (mg/mL) | Buffer | HCPs in product pool (ppm) | Monomer (%) in SEC | Step Yield (%) |
|---|---|---|---|---|
| 3.7 | Phosphate | 9 | 98.9 | 94.9 |
| 15.5 | Glycine/Succinate | 22.8 | 99.2 | 94.5 |
| 17.2 | Glycine/Succinate | 19.4 | 99.4 | 96.6 |
| 22.0 | Glycine/Succinate | 4 | 99.7 | 90.0 |

Approximately 700 ppm HCP in the protein A elution pools varying concentration of monoclonal antibodies. 0.75% caprylic acid was added, then the pH of the mixture was adjusted to 5.5 and the mixture was incubated at ambient temperature for 60 minutes. The precipitates were removed by sterile filtration.

Process Robustness

When developing industrial processes, it is valuable to identify a standard approach for processing a wide variety of antibodies. After the initial evaluation on one antibody, Applicants further integrated the CA-induced impurity precipitation process into several antibodies including IgG1 and IgG4 (Table 4). Although the optimal pH and CA concentration were slightly different for different antibodies, an operational pH range from 5.0 to 6.0 and CA concentration from 0.5 to 1.0% were identified for all five antibodies. The results in Table 4 show the HCP reduction, the percent monomer (SEC-HPLC) and yield achieved with five antibodies at the optimized pH and CA concentration. Of the five antibodies tested, four had more than 99% HCP reduction and the actual values were below 90 ppm. mAb IV is an IgG4 and the HCP reduction is 79%, lower than the other four antibodies. Product purity was slightly improved post precipitation with greater than 98% monomer in SEC-HPLC for four molecules. Product yield at the optimal pH and CA concentrations remained above 90% in majority of the cases with one exception at 82.8% (mAb III, IgG4). The Binding ELISA results for mAb II and mAb V showed that no activity compromise of the mAb II and mAb V purified by CA precipitation was observed.

TABLE 4

Effect of Caprylic Acid on Protein A Pool Impurity Reduction and Yield for Five Mabs

| Mab | Buffer | Optimal pH | CA (%) | Feed HCPs (ppm) | Elution HCPs (ppm) | HCPs removal (%) | SEC-Monomer (%) | Yield (%) | Binding ELISA (%) [a] |
|---|---|---|---|---|---|---|---|---|---|
| Mab I | Glycine/Succinate | 5.5 | 0.75 | 18224 | 88 | 99.9 | 98.2 | 95.1 | |
| Mab II | Glycine/Succinate | 5.5 | 0.75 | 700 | 1 | 99.8 | 99.7 | 98.1 | 86 [b] |
| Mab III | Glycine/Succinate | 5.5 | 0.50 | 5150 | 23 | 99.6 | 99.3 | 82.8 | |
| Mab IV | Glycine/Succinate | 6.0 | 1.00 | 2900 | 599 | 79.3 | 94.2 | 93.3 | |
| Mab V | Phosphate | 5.5 | 0.50 | 727 | 5 | 99.3 | 99.2 | 94.0 | 97 [c] |

[a] % binding compared to Reference Material. The specification of the relative binding activity of mAb to the reference material by ELISA method is 50-150%.
[b] The binding ELISA (%) for the mAb II control sample without CA precipitation is 89%.
[c] The binding ELISA (%) for the mAb V control sample without CA precipitation is 85%.

Removal of Caprylic Acid-Induced Precipitation

The data presented in the previous sections demonstrate the potential of using CA precipitation method as an effective antibody purification step. Implementation of protein A pool impurity precipitation with CA, however, would require a filtration step to remove the precipitants. In conventional processing, a substantial increase in turbidity is often observed upon neutralization of the low pH inactivated protein A column elution pool, which requires a filtration step to clarify solution prior to the following polishing step. As such, the antibody purification processes would not require additional depth filtration step in the CA precipitation since the depth filtration setting in the conventional process is used. Optimization of filter type for the removal of CA-induced impurity precipitation was done at lab scale using three types of filters, CORNING® 0.2-µm cup filter (Coring, cellulose acetate membrane, 13.6 cm²), Millipore Millistake depth filter (MCOHC, Millipore, 23 cm²), and 3 M ZETA PLUS® VR series filters (BC0025LVRO2 and BC0025LVR07, 3 M, 25 cm²), as shown in Table 5. The pressure drop threshold of 20 psig was set for testing the capacity of the filter. The control run using CORNING® 0.2-µm cup filter achieved a maximum pressure across the cup filter at a load of only 70 L/m². In contrast, all depth filters demonstrated capacities of >300 L/m². There was very little difference on depth filtration performance for HCP removal. Millipore Millistake and 3 M ZETA PLUS® VR 07 filters showed slight better HCP clearance than 3 M ZETA PLUS® VR 02 filters. 3 M ZETA PLUS® VR07 filter performance is comparable to Millipore Millistake depth filter. The depth filters were shown to have better performance and higher capacity than regular 0.2-µm membrane filter-Coring 0.2-µm cup filter.

ZETA PLUS® VR series filters have be validated and showed effective viral reduction (3 M application brief 2007) [25] and VR 07 filter offers more viral clearance capacity than VR 02 filter. Since the ZETA PLUS® VR 07 filter showed a higher or equivalent capacity compared with ZETA PLUS® VR 02 filter and Millipore Millistake MC0HC filter. ZETA PLUS® VR 07 was selected as the depth filter filtrate to remove CA precipitants.

TABLE 5

Comparison of Various Depth and Sterile Filters to Caprylic Acid Induced Impurity Precipitate Removal

| Filter | Membrane Area (cm²) | Max pressure (psi) | Capacity (L/m²) | Viral Clearance |
|---|---|---|---|---|
| CORNING ® sterile filter | 13.5 | >30 | 70 | NA |
| Millistake MCOH | 23 | <20 | 320 | NA |
| ZETA PLUS ® VR 02 | 25 | <20 | 320 | yes |
| ZETA PLUS ® VR 07 | 25 | <20 | 320 | yes |

NA: not available.

Residual Caprylic Acid Removal by Polishing Chromatography Step

Figure 6:
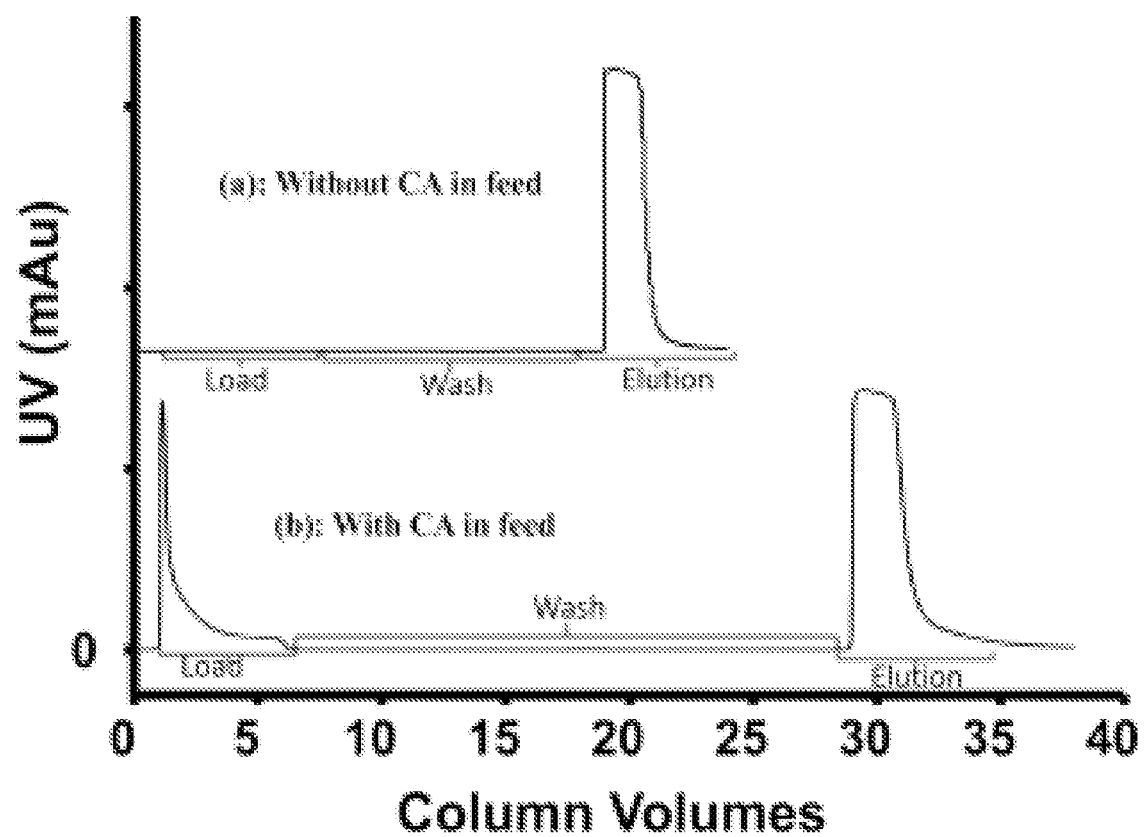
FIG. 6 shows CEX purification chromatogram loaded with filtered CA precipitation product pool.

In the previous studies, Applicants found that the amount of CA needed would not increase the conductivity of product pool which allows the product to be loaded directly onto an ion exchange column without pH and conductivity adjustment. To remove the residual CA and other impurities, a CEX column as a polishing column step was evaluated. Purification runs were performed at lab scale with approximately 0.5-1 L of filtered product pool with residual CA. Post ZETA PLUS® VR 07 filter filtration, approximately 2-5-folds of CA were removed (data not shown). Approximately 1.5 mg/mL of residual CA were remained in the filtered product pool. The filtered product pool was processed through a CEX chromatography column to evaluate the overall process performance. FIG. 6 showed that no major impact was observed on the chromatographic behavior of mAb with CA in the load. A sharp breakthrough peak in the flow through was observed. Post washing, the antibody was eluted from the column using elution buffer and the elution peak was shown in the chromatogram. The fractions from flowthrough, wash and elution were collected and analyzed. The peaks in flowthrough and wash fractions contain CA with little amount of proteins. The elution peak contains antibody. Under these conditions, more than 50% CA flowed through on the CEX column, while mAb bound onto the CEX column and eluted from the column.

Applicants also tested the CEX performance by loading a filtered product pool with 1% CA spiking in before loading, 1% of CA concentration in the feed did also not show the change in the binding behavior of antibody on the POROS® XS CEX column.

The results of the studies shown in Table 6 demonstrated that CEX purification of filtered CA-induced impurity precipitation pool reduces residual CA to low levels <400 µg/mL. The recovery of CEX step was approximately 84%. The monomer (%; SEC-HPLC) is greater than 99%. HCPs, DNA, and other impurities were in undetectable levels.

TABLE 6

Two-Chromatography Step Process Performance with Optimized Caprylic Acid Precipitation Conditions

| Step | Total CA (mg) | CA (%) | Residual CA (mg/mL) | Residual CA (µg/mg mAb) | Yield (%) | SEC-monomer (%) | HCPs (ng/mL) | DNA (pg/mL) |
|---|---|---|---|---|---|---|---|---|
| Load | 155.7 | 100 | 5.6 | 429 | | | | |
| Flowthrough | 58.8 | 38.0 | 2.1 | 2140 | | | | |
| Wash | 52.1 | 33.5 | 2.0 | >40000 | | | | |
| Elution | 13.9 | 8.9 | <0.4 | 165 | 84.1 | 99.0 | ND | ND |

0.75% CA was added into the mAb II Protein A elution pool and the pH was adjusted to 5.5. After mixing for 60 min, the pool was passed through ZETA PLUS ® VR07 filter. The filtrate pool was loaded onto the prepacked CEX column (POROS ® XS, 1.2 cm × 5 cm = 5.7 mL). The load, flowthrough, wash, and elution fractions were analyzed by HCP- ELISA, SEC, Protein A titer, qPCR, and CA-RP-HPLC assays.
ND: not detected. CA: caprylic acid.

Historically, sodium caprylate (salt form of CA) has been used in preparation of therapeutic human serum albumin for over 50 years. The intravenous administration of large volumes of albumin formulated in 20 mM (3.32 mg/mL) caprylate over an extended period of time have been tested and showed no toxic to the human [20]. The CA concentration in the formulated therapeutical albumin is eightfold higher than that in the CEX elution pool. It was also shown that caprylate was nontoxic at the injection of 600-mg caprylate per kilogram of mice body weight [22]. Therefore, the risk for the implementation of CA precipitation step in the manufacturing process is relative low.

To compare the performance of two-chromatography-step process including CA precipitation with the typical three-chromatography-step process, the process yields, and product quality (HCPs, SEC monomer %) for each unit operation step are monitored and shown in Table 7. Clarified mAb I cell CB material was processed in the following order for two-chromatography-step process: Harvest→Protein A→0.0.75% CA addition and adjust pH to 5.0→sterile filtration→CEX; and processed in the following order for three-chromatography-step process: Harvest→Protein A→adjust pH to 7.2→sterile filtration→flow through (F/T) anion exchange membrane column (AEX)→CEX. CA precipitation is much more effective than flow through AEX in HCP removal. Under the CA precipitation of Protein A elution pools, the HCPs and SEC monomer % in the filtered CA precipitation pool were lowered to acceptable levels. However, the HCPs in the AEX-F/T pool still remained approximately 300 ppm which were further reduced down to acceptable levels by the third column (CEX) in this three-chromatography-step process. Monomer % in SEC and yields with two-chromatography-step process in combination with CA precipitation are comparable with that of three-chromatography-step process without CA precipitation. These data suggested that CA precipitation could replace a polishing column step in a standard three-chromatography-step process.

the most typical. By focusing on the possible action mechanisms of the precipitating agent, there are two different models: (1) interaction with the solvent in which precipitation takes place because of salting out (typically with a multivalent salt), whereby the salt "sequesters" water molecules from the protein surface, or (2) interaction with the protein in which precipitation is caused by the binding of a ligand that then increases the interfacial hydrophobic character of the protein surface or by crosslinking. Morais and Massaldi [19] have recently proposed a mechanistic model for the action of CA to precipitate plasma proteins, where direct interaction between albumin and CA takes place. They also found a mass ratio of CA to albumin about 1 to be optimal for maximum precipitation and purity of the remaining IgGs at any dilution.

Figure 7:
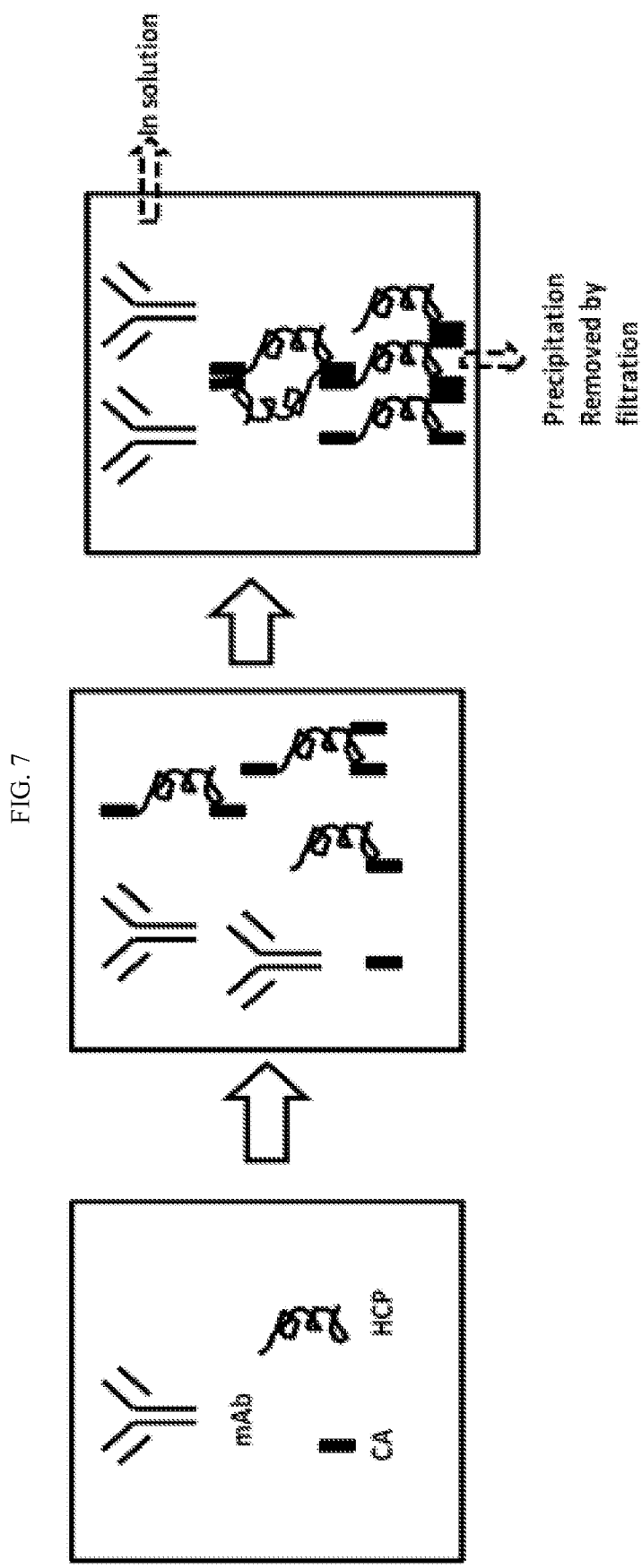
FIG. 7 shows schematic diagram of the proposed model for HCP precipitation by CA during the antibody purification process.

Tables 3 and 4 have shown that both antibody recovery and quality are independent from the antibody concentrations (from 4 to 22 mg/mL) and antibody molecules. More than 99% of HCPs in the Protein A elution pool were precipitated by CA and then removed by filtration for all of the mAbs tested, except mAb IV (approximately 79% HCPs was removed for mAb IV). These results imply that the CA molecules uptake HCPs under precipitation, not IgG. The possible mechanism for the CA-induced impurity precipitation is presented in FIG. 7. The CA molecules first bind to HCPs through binding site on the surface which elicits conformational changes of the HCP molecules and more binding sites are exposed. Then the CA molecules continue to incorporate into the original and newly created sites on the macromolecular complex in the form of micelle-like structures that create bridges among complexes, until a cascade precipitation takes place. The antibodies do not interact with CA and remain in the solution.

Potential Viral Clearance Capability

When removing a chromatography step from a three-chromatography-step purification process, viral clearance is

TABLE 7

Comparison of the Process Performances of the Two-Column Process with the Typical Three-Column Process

| Three-column process | | | | Two-column process | | | |
|---|---|---|---|---|---|---|---|
| Unit Operation Step | HCPs (ppm) | SEC (monomer %) | Yield (%) | Unit Operation Step | HCPs (ppm) | SEC (monomer %) | Yield (%) |
| Protein A Elution | 7996 | 97.3 | 99.9 | Protein A Elution | 7996 | 97.3 | 99.9 |
| VIN Bulk, pH 7.2 | 501 | 97.8 | 97.3 | VIN Bulk, 0.75% CA, pH 5.5 | 27 | 98.2 | 95.1 |
| AEX-F/T | 300 | 97.8 | 99.0 | | | | |
| CEX-Elution | <1 | 98.0 | 90.0 | CEX-Elution | <1 | 98.6 | 89.0 | mAb I Protein A pool was purified using a typical three-chromatography-step process including two-polishing column steps (AEX-F/T mode and CEX B/E mode), developed for purifying mAb I and also a two-chromatography-step process including 0.75% (v/v) CA precipitation of the protein A elution pool.

Potential Mechanism for Protein Precipitation by CA

The mechanism of CA precipitation of serum protein has not been clearly established yet, although several proposals have been made by studying the interaction between CA and protein molecules [26-28]. Among these studies, dehydration of the outer shell layer of the protein by the addition of a salt (salting out) and the formation of complexes by crosslinking or electrostatic-hydrophobic interactions are another critical quality attribute to consider according to the risk assessment. The two-chromatography process should be designed to have sufficient viral removal and inactivation capability. For over 50 years, CA has been added to human albumin as a stabilizer during heat treatment, a process developed to inactivate hepatitis viruses [7, 8, 14, 20, 24]. CA has been used to precipitate non-immunoglobulin proteins from human plasma. It has been reported to be an effective agent in inactivating viruses in protein derived from plasma or cell cultures [7, 8, 14, 20, 24]. Addition of CA to a concentration of 50 mM in 1 h resulted in the complete inactivation of bovine viral diarrhea virus (5-8 log 10) [8]. Caprylate was effective against the human pathogen human immunodeficiency virus type-1 (HIV-1) as well as pseudorabies virus (PRV) [24]. Enveloped virus inactivation by CA is considered to occur when the lipophilic, nonionized form of CA partitions into the viral lipid membrane [24]. CA has been shown the ability to be effective/robust against lipid-enveloped viruses of varying size, shapes, and nucleic acid content [8, 14, 24]. It is active over a range of concentration and temperatures, and can be used when manufacturing proteins with different physicochemical properties. CA precipitation was previously shown to be an effective method to precipitate xMuLV virus and consequently remove the virus by the 0.45-μm filtration using the RT-qPCR method [8, 14, 24]. CA has demonstrated the capability for viral clearance. Therefore, implementing CA precipitation method at pH 5-6 in the neutralization step post low pH (normally pH 3-4) VI would add an orthogonal viral clearance method which can possibly claimed in addition to the commonly used low pH (3-4) VI in the typical downstream purification process. In addition, 3 M ZETA PLUS® VR series filter [25] was previously reported to be effective in retaining various viruses including BVD, EMC, HIV, PPV, and PRV through the ion exchange capture mechanism. FDA recommends that multiple viral clearance steps operated by different mechanisms, be used in biopharmaceutical processes. ZETA PLUS® VR series filter, acting as an AEX membrane chromatography can be complementary to other viral clearance steps, such as chromatography separation (protein A column purification and cation exchange column purification), size-exclusion viral filtration, VI (low pH 3-4) and neutralization of VI pool with CA precipitation.

Manufacturing Capability Consideration

Precipitation of impurities with CA post protein A column purification provides an alternative to polishing chromatography step for mAb purification. It can be implemented in a VI product pool tank. Since precipitation can be carried out in existing tanks in manufacturing operations, facility space could be saved, and there is no need for substantial capital investments.

Because the CA precipitation is performed in the neutralization step after low pH VI (FIG. 1), it does not require an extra unit operation. The processing time is minimal, much shorter than an anion exchange chromatography step. Compared with flow through AEX, CA precipitation is more effective in HCP removal for the conditions and proteins evaluated in the studies (Table 7). Additionally, the precipitation step requires a small volume addition of CA which would reduce buffer consumption compared to a chromatography step. The process volumes required for the addition of CA can be managed in a relatively small disposable biobag at commercial scale.

This study indicated that the CA precipitation process is also insensitive to the temperature between 15 and 25° C. Since the manufacturing facility temperature is controlled at approximately 22° C., the caprylic-induced impurity precipitation is robust in manufacturing production.

CA precipitation is effective for multiple antibody molecules demonstrating the capability of this technique to become a part of a generic purification process. CA is an inexpensive raw material even when compared to chromatography resins used over hundreds of cycles. This method makes it possible to operate at a very large scale, requiring short processing time and minimal buffer preparation. Moreover, CA has the additional advantages of low toxicity and simplicity. It is active over mAbs with a wide range of pIs and can be used when manufacturing antibodies with different physicochemical properties.

Conclusions

In combination with a Protein A capture step and an ion exchange polishing step, operated in bind and elute mode, CA precipitation enables a two column purification process with minimal development (FIG. 1). Since the optimal pH of CA-induced impurity precipitation is from 5 to 6 for most of mAb, the cation exchange column is the preferred polishing step in order to simplify binding behavior (directly loading onto the CEX column without additional pH or conductivity adjustment) and ensure removal of CA prior to viral filtration. CA-induced precipitation of impurities after the protein A column provides clearance of HCPs and HMW aggregates, which is equivalent or superior to a polishing chromatography step. Impurities are removed to acceptable levels for clinical material production for all of tested antibodies. Possible viral clearance can be achieved through CA precipitation at pH 5-6. This would add an additional orthogonal viral clearance approach in mAb purification process.

Residual CA was removed from the process by the bind and elute chromatography step. It is anticipated that use of this two-column downstream process with CA precipitation will further enhance the speed of development. This will facilitate further reduction in the process time and resources required for the introduction of mAbs drug candidates into clinical trials. Finally, CA precipitation in the antibody purification process has demonstrated to be an effective alternative to a column chromatography step which can lead to significant savings.

Literature Cited

1. Gottschalk U. Bioseparation in antibody manufacturing: the good, the bad and the ugly. *Biotechnol Prog.* 2008; 24: 496-503.
2. Hober S., Nord K. & Linhult M. Protein A chromatography for antibody purification. *J. Chromatogr B*, 2007; 848: 40-47.
3. Low D, O'Leary R, & Pujar N. Future of antibody purification. *J Chromatogr, B,* 2007; 848: 48-63.
4. Shukla A, Hubbard B, Tressel T, Guhan S & Low D. Downsteam processing of monoclonal antibodies-Application of platform approaches. *J Chromatogr B.* 2007; 848: 28-39.
5. Atha D. H. & Ingham K. C. Mechanism of precipitation of proteins by polyethylene glycols. *J. Biol. Chem.* 1981; 256(23): 12108-12117.
6. Bernard N, Jolivalt C & Schwartzentruber J. Protein precipitation by caprylic acid: equilibrium composition data. *Biotechnol Bioeng.* 1996; 49: 405-411.
7. Brodsky Y., Zhang C., Yigzaw Y. & Vedantham G. Caprylic acid precipitation method for impurity reduction: An alternative to conventional chromatography for monoclonal antibody purification. *Biotechnol Bioeng.* 2012; 109(10): 2589-2598.
8. Johnston A., Uren E., Johnstone D. & Wu J. Low pH, caprylate incubation as a second viral inactivation step in the manufacture of albumin parametric and validation studies. *Biologicals,* 2003; 31: 213-221.
9. Ko K. Y., & Ahn D. U. Preparation of immunoglobulin Y from egg yolk using ammonium sulfate precipitation and ion exchange chromatography, *Poultry Science,* 2007; 86(2): 400-407.

10. Kumar V., Dixit N., Singh S. N. & Kalonia D. S. Phase separation of proteins by polyethylene glycols: Implications in preformulation and early stage formulation development. *American Pharmaceutical Review-The Review of American Pharmaceutical Business & Technology.*, 2011; Nov. 1.
11. Mahn A., & Ismail M. Depletion of highly abundant proteins in blood plasma by ammonium sulfate precipitation for 2D-PAGE analysis. *J Chromatrogr B, Analytical Technologies in the biomedical and life sciences,* 2011; 879(30): 3645-8.
12. McKinney M., & Parkinson A. A simple, non-chromatographic procedure to purify immunoglobulins from serum and ascites fluid. *J. Immunol. Methods,* 1987; 96: 271-278.
13. Moore P. A., & Kery V. High-throughput protein concentration and buffer exchange: comparison of ultrafiltration and ammonium sulfate precipitation. *Methods in Molecular Biology.* 2009; 498: 309-14.
14. Parkkinen J., Rahola A., Bonsdorff L. V., Torma T. E. A modified caprylic acid method for manufacturing immunoglobulin G from human plasma with high yield and efficient virus clearance. *Vox Sang.* 2006; 90: 97-104.
15. Park J. W., Lee S. G., Song J. Y., Joo J. S., Chung M. J., Kim S. C., Youn H. S., Kang H. L., Baik S. C., Lee W. K., Cho M. J., & Rhee K H. Proteomic analysis of *Helicobacter pylori* cellular proteins fractionated by ammonium sulfate precipitation. *Electrophoresis.* 2008; 29(13): 2891-903.
16. Robinson M. W., Scott D. G. I., Bacon P. A., Walton K. W., Coppock J. S. & Scott D. L. What proteins are present in polyethylene glycol precipitates from rheumatic sera. *Annals of the Rheumatic Diseases.* 1989; 48: 496-501.
17. Van Oss C. J. On the mechanism of the cold ethanol precipitation method of plasma protein fractionation. *J Protein Chem.* 1989; 8(5): 661-68.
18. Yoshikawa H., Hirano A., Arakawa T. & Shiraki K. Mechanistic insights into protein precipitation by alcohol. *International J Biolog Macromol.* 2012; 50: 865-871.
19. Morais V. & Massaldi H. A model mechanism for protein purification by caprylic acid: application to plasma purification. *Biotechnology and Applied Biochemistry.* 2012; 59(1): 50-54.
20. Gellis S. S., Neefe J. R., Lawrence J. S. Jr., Strong E., Janeway C. A. & Scatchard G. Chemical, clinical, and immunological studies on the products of human plasma fractionation. XXXVI. Inactivation of the virus of homologous serum hepatitis in solutions of normal human serum albumin by means of heat. *J Clin Invest.* 1948; 27: 239-244.
21. Yu M. W. & Finlayson J. S. Stabilization of human albumin by caprylate and acetyltryptophanate. *Vox Sang.* 1984; 47(1): 28-40.
22. Oro L. & Wretlund A. Pharmacological effects of fatty acids, triolein and cotton seed oil. *Acta Pharmachol Toxicol.* 1961; 18:141-152.
23. Swinnen, K., Krul, A., Goidsenhoven, I. V., Tichelt, N. V., Roosen, A., Houdt, K. V., Performance comparison of protein A affinity resins for the purification of monoclonal antibodies, *J. Chromatogr.*, B. 2007; 848: 97-107.
24. Korneyeva M., Hotta J., Lebing W., Rosenthal R. S., Franks L. & Petteway Jr S. R. Enveloped virus inactivation by caprylate: a robust alternative to solvent-detergent treatment in plasma derived intermediates. *Biologicals,* 2002; 30: 153-162.
25. CUNO Application Brief. CUNO ZETA PLUS® VR filters for viral reduction in biopharmaceutical processes. April, 2002; www.cuno.com.
26. Steinbuch, M. and Audran, R., The isolation of IgG from mammalian sera with the acid of caprylic acid, *Arch. Biochem. Biphys.*, 1969, 134: 279-284.
27. Boyer, P. D., Ballou, G. A., and Luck, J. M. The combination of fatty acids and released compounds with serum albumin: III. The nature and extent of the combination, *J Biol. Chem.*, 1947, 167: 407-424.
28. Van Oss C. J. Good, R. J. and Chaudhury, M. K., Solubility of proteins, *J Protein Chem.* 1986; 5: 385-405.

EQUIVALENTS

Those skilled in the art will recognize or be able to ascertain using no more than routine experimentation, many equivalents of the specific embodiments of the invention described herein. Such equivalents are intended to be encompassed by the following claims.

INCORPORATION BY REFERENCE

All patents, pending patent applications, and other publications cited herein are hereby incorporated by reference in their entireties.

We claim:

1. A method of purifying a protein of interest from a mixture which comprises the protein of interest and one or more contaminants, comprising:
    a) subjecting the mixture to a first chromatography step, wherein the first chromatography is a protein A affinity chromatography;
    b) recovering the protein of interest in an elution solution having a low pH between 2.5 and 4;
    c) adding caprylic acid to the elution solution and then adjusting the pH to at least 5.5 to form a contaminant precipitate, wherein the final concentration of the caprylic acid is between about 0.5 and 1% (v/v);
    d) removing the contaminant precipitate from the elution solution; and
    e) subjecting the post-precipitated elution solution to a second chromatography column, wherein the second chromatography is an ion exchange chromatography, thereby purifying the protein of interest.
2. The method of claim 1, wherein the contaminants are selected from host cell proteins, host cell metabolites, host cell constitutive proteins, nucleic acids, endotoxins, viruses, product related contaminants, lipids, media additives and media derivatives.
3. The method of claim 1, wherein the second chromatography is a cation exchange chromatography.
4. The method of claim 1, wherein the second chromatography is an anion exchange chromatography.
5. The method of claim 1, wherein the contaminant precipitate is removed by centrifugation, sterile filtration, depth filtration or tangential flow filtration.
6. The method of claim 1, wherein the final concentration of the caprylic acid is about 0.5%, 0.75% or 1% (v/v).
7. The method of claim 1, wherein the mixture is not subjected to an additional chromatography step.
8. The method of claim 1, wherein the mixture is selected from a harvested cell culture fluid, a cell culture supernatant, and a conditioned cell culture supernatant, a cell lysate, and a clarified bulk.
9. The method of claim 8, wherein the cell culture is a mammalian cell culture.

10. The method of claim 1, wherein the protein of interest is an antibody.

11. The method of claim 1, wherein the final concentration of the caprylic acid is about 0.75% (v/v) and the pH is adjusted to at least 5.5.

* * * * *